US010598596B1

(12) United States Patent
Hug et al.

(10) Patent No.: US 10,598,596 B1
(45) Date of Patent: Mar. 24, 2020

(54) NATIVE FLUORESCENCE DETECTION METHODS, DEVICES, AND SYSTEMS FOR ORGANIC COMPOUNDS

(71) Applicant: Photon Systems, Inc., Covina, CA (US)

(72) Inventors: William F. Hug, Altadena, CA (US); Rohit Bhartia, Pasadena, CA (US); Ray D. Reid, Glendora, CA (US); Arthur L. Lane, Arcadia, CA (US)

(73) Assignee: Photon Systems, Inc., Covina, CA (US)

(*) Notice: Subject to any disclaimer, the term of this patent is extended or adjusted under 35 U.S.C. 154(b) by 0 days.

(21) Appl. No.: 16/362,453

(22) Filed: Mar. 22, 2019

Related U.S. Application Data

(63) Continuation of application No. 15/909,260, filed on Mar. 1, 2018, which is a continuation of application (Continued)

(51) Int. Cl.
 *G01N 21/64* (2006.01)
 *G01J 3/10* (2006.01)
 (Continued)

(52) U.S. Cl.
 CPC ............... *G01N 21/64* (2013.01); *G01J 3/10* (2013.01); *G01J 3/36* (2013.01); *G01J 3/44* (2013.01);
 (Continued)

(58) Field of Classification Search
 CPC .......... G01N 21/65; G01N 2021/6471; G01N 2021/6421; G01N 21/645; G01N 21/6456
 See application file for complete search history.

(56) References Cited

U.S. PATENT DOCUMENTS 3,505,613 A   4/1970 Campbell et al.
3,646,476 A   2/1972 Barker et al.
(Continued)

OTHER PUBLICATIONS

Bhartia, W. F. Hug, E. C. Salas, R. D. Reid, K. K. Sijapati, A. Tsapin, W. Abbey, P. G. Conrad, K. H. Nealson and A. L. Lane, "Classification of Organic and Biological materials with Deep UV Excitation", Applied Spectroscopy, vol. 62, No. 10, Oct. 2008.
(Continued)

*Primary Examiner* — David P Porta
*Assistant Examiner* — Fani Boosalis
(74) *Attorney, Agent, or Firm* — Dennis R. Smalley

(57) ABSTRACT

Naphthalene, benzene, toluene, xylene, and other volatile organic compounds VOCs have been identified as serious health hazards. Embodiments of the invention are directed to methods and apparatus for near-real-time in-situ detection and accumulated dose measurement of exposure to naphthalene vapor and other hazardous gaseous VOCs. The methods and apparatus employ excitation of fluorophors native or endogenous to compounds of interest using light sources emitting in the ultraviolet below 300 nm and measurement of native fluorescence emissions in distinct wavebands above the excitation wavelength. The apparatus of some embodiments are cell-phone-sized sensor/dosimeter "badges" to be worn by personnel potentially exposed to hazardous VOCs. The badge sensor of some embodiments provides both real time detection and data logging of exposure to naphthalene or other VOCs of interest from which both instantaneous and accumulated dose can be determined.

19 Claims, 8 Drawing Sheets

Related U.S. Application Data

No. 15/263,063, filed on Sep. 12, 2016, now Pat. No. 9,909,990, which is a continuation of application No. 14/313,994, filed on Jun. 24, 2014, now Pat. No. 9,442,070, which is a continuation-in-part of application No. 12/628,205, filed on Nov. 30, 2009, now Pat. No. 8,759,791.

(60) Provisional application No. 61/118,591, filed on Nov. 28, 2008.

(51) Int. Cl.

| | | |
|---|---|---|
| *G01N 21/88* | (2006.01) | |
| *G01J 3/44* | (2006.01) | |
| *G01J 3/36* | (2006.01) | |
| *G01N 33/00* | (2006.01) | |
| *G01N 21/65* | (2006.01) | |
| *G01N 27/447* | (2006.01) | |

(52) U.S. Cl.
CPC ..... *G01N 21/6486* (2013.01); *G01N 21/8806* (2013.01); *G01N 21/65* (2013.01); *G01N 27/44721* (2013.01); *G01N 33/0047* (2013.01); *G01N 2021/6421* (2013.01); *G01N 2021/6471* (2013.01); *G01N 2201/062* (2013.01); *G01N 2201/0612* (2013.01); *G01N 2201/06113* (2013.01); *G01N 2201/126* (2013.01)

(56) References Cited

U.S. PATENT DOCUMENTS

| | | |
|---|---|---|
| 3,757,250 A | 9/1973 | Campbell et al. |
| 3,891,943 A | 6/1975 | Dowley et al. |
| 4,085,385 A | 4/1978 | Fein et al. |
| 4,380,078 A | 4/1983 | Wang et al. |
| 4,641,313 A | 2/1987 | Tobin et al. |
| 4,714,860 A | 12/1987 | Brown et al. |
| 4,730,334 A | 3/1988 | Collins et al. |
| 4,821,281 A | 4/1989 | Lind et al. |
| 4,953,176 A | 8/1990 | Ekstrand |
| 5,088,820 A | 2/1992 | Winefordner et al. |
| 5,194,912 A | 3/1993 | Batchelder et al. |
| 5,311,529 A | 5/1994 | Hug |
| 5,440,579 A | 8/1995 | Molva et al. |
| 5,442,438 A | 8/1995 | Batchelder et al. |
| 5,465,607 A | 11/1995 | Corrigan et al. |
| 5,623,342 A | 4/1997 | Baldwin et al. |
| 5,677,923 A | 10/1997 | Rice et al. |
| 5,807,764 A | 9/1998 | Rice et al. |
| 6,002,476 A | 12/1999 | Treado |
| 6,287,869 B1 | 9/2001 | Hug et al. |
| 6,693,944 B1 | 2/2004 | Hug et al. |
| 6,891,618 B2 | 5/2005 | Harju et al. |
| 7,084,972 B2 | 8/2006 | Treado |
| 7,138,648 B2 | 11/2006 | Kneissl et al. |
| 7,154,595 B2 | 12/2006 | Paldus et al. |
| 7,245,369 B2 | 7/2007 | Wang et al. |
| 7,286,231 B2 | 10/2007 | Maier et al. |
| 7,399,958 B2 | 7/2008 | Miller et al. |
| 7,525,653 B1 | 4/2009 | Hug et al. |
| 7,564,541 B2 | 7/2009 | Tuschel |
| 7,590,161 B1 | 9/2009 | Hug et al. |
| 7,595,473 B2 | 9/2009 | Walt et al. |
| 7,800,753 B1 | 9/2010 | Hug et al. |
| 7,817,273 B2 | 10/2010 | Bahatt et al. |
| 7,956,991 B2 | 6/2011 | Bangalore et al. |
| 8,395,770 B1 | 3/2013 | Hug et al. |
| 8,759,791 B1 | 6/2014 | Hug et al. |
| 9,442,070 B1 | 9/2016 | Hug et al. |
| 9,568,418 B1 | 2/2017 | Hug et al. |
| 9,909,990 B1 | 3/2018 | Hug et al. |
| 9,915,603 B1 | 3/2018 | Hug et al. |
| 2006/0008866 A1 | 1/2006 | Flick et al. |
| 2007/0081156 A1 | 4/2007 | Treado et al. |
| 2011/0003279 A1 | 1/2011 | Patel |

OTHER PUBLICATIONS

Gregg, S.D., J.L.Campbell, J.W. Fisher, and M.G. Bartlett, "Methods for characterization of Jet Propellant-8: vapor and aerosol", Biomed. Chromatograph. 21, pp. 463-472, Mar. 2007.

Ianoul, A., T. Coleman, and S.A. Asher, "UV Resonance Raman Spectroscopic Detection of Nitrate and Nitrite in Wastewater Treatment Processes", Anal. Chem., vol. 74, pp. 1458-1461, 2002.

Jenkins, F.A. and H.E. White, Fundamentals of Optics, (McGraw Hill), 1957.

Macleod, A., "Thin-Film Optical Filters", McGraw-Hill, ISBN#0-07-044694-6, reprinted 1989.

McCreery, R.L., "Raman Spectrocopy for Chemical Analysis", John Wiley & Sons, ISBN # 0-471-25287-5, 2000.

Military Standardization Handbook, MIL-HDBK-141, Section 20, Oct. 5, 1962. (angle dependence, p. 20-11).

Munro, C.H., V. Pajcini, and S.A. Asher, "Dielectric Stack Filters for Ex Situ and In Situ UV Optical-Fiber Probe Raman Spectroscopic Measurements", App. Spect., vol. 51, No. 11, pp. 1722-1729, 1997.

Pleil, J.D., Smith, L.B., Zelnick, S.D., "Personal exposure to JP-8 jet fuel vapors and exhaust at Air Force Bases", Environmental Health Perspectives, v108, n3 p. 183-192 (2000).

R. Bhartia, W. F. Hug, E. C. Salas, K. Sijapati, A. L. Lane, R. D. Reid and P.G.Conrad, "Biochemical detection and identification false alarm rate: dependence on wavelength using laser induced native fluorescence", Proc. SPIE, vol. 6218, Orlando, FL. Apr. 2006.

S. A. Asher, C.R. Johnson, "Raman Spectroscopy of a Coal Liquid Shows That Fluorescence Interference Is Minimized with Ultraviolet Excitation", Science, 225, 311-313, Jul. 20, 1984.

Sparrow, M.C., J.F. Jackovitz, C.H. Munro, W.F. Hug, and S.A. Asher, "A New 224nm Hollow Cathode UV Laser Raman Spectrometer", J. App. Spectroscopy, vol. 55, No. 1, Jan. 2001.

Storrie-Lombardi, M. C., W. F. Hug, G. D. McDonald, A. I. Tsapin, and K. H. Nealson. "Hollow cathode ion laser for deep ultraviolet Raman spectroscopy and fluorescence imaging". Rev. Sci. Instruments, 12, 4452-4459, Dec. 2000.

W. H. Hug, R. Bhartia, A.Tsapin, A.L.Lane, P.G.Conrad, K. Sigapati, and R.D. Reid, "Status of Miniature Integrated UV Resonance Fluorescence and Raman Sensors for Detection and Identification of Biochemical Warfare Agents", Proc. SPIE, vol. 5994, p. 5884J1-12, Boston, MA. Oct. 2005.

Wolf, W.L.ed., Handbook of Military Infrared Technology, Office of Naval Research, Dept. of the Navy, Washington, D. C., pp. 286-306, 1965.

Arslanbekov, et al., "Self-consistent Model of High Current Density Segmented Hollow Cathode Discharges", J. App. Phys., vol. 81, No. 2, (Jan. 1997): pp. 1-15.

Asher, S.A., "Resonance Raman Spectroscopy of Hemoglobin", Methods in Enzymology, vol. 76, (1981): pp. 371-413.

Asher, S.A., "UV Resonance Raman Spectroscopy for Analytical, Physical, and Biophysical Chemistry, Part 1", Anal. Chem., vol. 65, No. 2, (Jan. 15, 1993): pp. 59-66.

Asher, S.A., "UV Resonance Raman Spectroscopy for Analytical, Physical, and Biophysical Chemistry, Part 2", Anal. Chem., vol. 65, No. 4, (Feb. 15, 1993): pp. 201-210.

Asher, S.A., "UV Resonance Raman Studies of Molecular Structure and Dynamics: Applications in Physical and Biophysical Chemistry", Ann. Rev. Phys. Chem., vol. 39, (1988): pp. 537-588.

Asher, S.A., et al., "Development of a New UV Resonance Raman Spectrometer for the 217-400 nm Spectral Region", Rev. Sci. Instr. vol. 54, (Dec. 1983): pp. 1657-1662.

Cho, N., and S.A. Asher, "UV Resonance Raman and Absorption Studies of Angiotensin II Conformation in Lipid Environments", Biospectroscopy, vol. 2, (1996): pp. 71-82.

Cho, N., Song, S., and S.A. Asher, "UV Resonance Raman and Excited-State Relaxation Rate Studies of Hemoglobin", Biochemistry, vol. 33, (1994): pp. 5932-5941.

(56) References Cited

OTHER PUBLICATIONS

Gerstenberger, et al., "Hollow Cathode Metal Ion Lasers", IEEE J. Quantum Elect., vol. QE 16, No. 8, (Aug. 1980): pp. 820-834.
McNeil, et al., "Ultraviolet Laser Action From Cu II in the 2500-A Region", Appl. Phys. Letters, vol. 28, No. 4, (Feb. 15, 1976): pp. 207-209.
Milofsky, R. E., et al., "Native Fluorescence Detection of Nucleic Acids and DNA Restriction Fragments in Capillary Electrophoresis", Anal. Chem., vol. 65, (Jan. 1993): pp. 153-157.
Solanki, et al., "Multiwatt Operation of Cu II and Ag II Hollow Cathode Lasers", IEEE J. Quant. Elect., vol. QE-16, No. 12, (Dec. 1980); pp. 1292-1294.
Warner, et al., "Metal-Vapor Production by Sputtering in a Hollow-Cathode Discharge: Theory and Experiment", J. App. Phys., vol. 50, No. 9, (Sep. 1979): pp. 5694-5703.
Chi, Z., et al., "UV Resonance Raman-Selective Amide Vibrational Enhancement: Quantitative Methodology for Determining Protein Secondary Structure", Biochemistry, vol. 37, (1998): pp. 2854-2864.

NATIVE FLUORESCENCE DETECTION METHODS, DEVICES, AND SYSTEMS FOR ORGANIC COMPOUNDS

RELATED APPLICATIONS

This application is a continuation of U.S. patent application Ser. No. 15/909,260, filed on Mar. 1, 2018 which is a continuation of U.S. patent application Ser. No. 15/263,063, filed on Sep. 12, 2016, now U.S. Pat. No. 9,909,990, which is a continuation of U.S. patent application Ser. No. 14/313,994, filed on Jun. 24, 2014, now U.S. Pat. No. 9,442,070, which in turn is a continuation-in-part of U.S. patent application Ser. No. 12/628,205, filed on Nov. 30, 2009, now U.S. Pat. No. 8,759,791, which claims benefit of U.S. Patent Application No. 61/118,591, filed on Nov. 28, 2008. Each of these applications is incorporated herein by reference as if set forth in full herein.

This application also incorporates by references the teachings in the following patent applications: (1) U.S. patent application Ser. No. 12/545,772, filed on Aug. 21, 2009, now U.S. Pat. No. 8,395,770, (2) U.S. patent application Ser. No. 12/399,743, filed on Mar. 6, 2009, and (3) U.S. Provisional Application No. 60/616,269, filed on Oct. 5, 2004.

U.S. GOVERNMENT RIGHTS

One or more of the inventions set forth herein were made with U.S. Government support under one or more of (1) NASA Contract No. NAS2-02086, (2) DARPA Contract No. W31P4Q-04-C-R039, and (3) U.S. Army SBIR Contract No. W911NF-09-C-0038. The Government has certain rights to these inventions.

FIELD OF THE INVENTION

The field of the invention is in situ, reagentless, compact sensors for detection and classification of organic compounds (e.g. atmospheric vapors, including volatile organic compounds (VOCs), or solid or liquid materials located on surfaces), and more particularly sensors and methods that use ultraviolet excitation of fluorophors in the compounds of interest and detection of resulting fluorescence.

BACKGROUND OF THE INVENTION

VOCs are common material components of the atmosphere with many sources. Common sources include fueling stations for vehicles, industrial and commercial degreasers, paint shops, and other sources. These VOCs include compounds such as mono and polycyclic aromatic hydrocarbons (e.g., benzene, toluene, xylene, naphthalene, etc.), halogenated hydrocarbons (e.g., trichloroethylene (TCE), carbon tetrachloride (CT)), and aliphatic hydrocarbons (e.g., hexane or octane)

A wide array of sensors have been developed and are commercially available to detect and quantify the amount and type of VOCs for use by workers, first responders, and others involved in safety inspection or handling of these materials. Several methods are employed in commercially available sensors including: photoionization detection (PID); flame ionization detection (FID); non-dispersive IR/absorption detection (NDIR); thermal conductivity (TC); hot wire or hot semiconductor detection; and electrochemical detection. None of these methods is specific to naphthalene, benzene, toluene, xylene, and several other hazardous VOCs.

Naphthalene exposure to personnel working in the vicinity of JP8 or other naphthalene-bearing jet fuels has been shown to cause physical damage to lung tissue and potentially cause genetic damage under prolonged exposure as noted in Herrin, B. R., Haley, J. E., Lantz, R. C., Witten, M. L., "A reevaluation of the threshold exposure level of inhaled JP-8 in Mice", Journal of Toxicological Sciences, v 31 3; p 219 (2006) and in Schreiner, C. A., "Genetic Toxicity of Naphthalene: A Review", Journal of Toxicology and Environmental Health, Part B, v6 p 161 (2003). Exposure to naphthalene may occur through inhalation and dermal contact as noted in Egeghy, P. P., L. Hauf-Cabalo, R. Gibson, and S. M. Rappaport. "Benzene and naphthalene in air and breath as indicators of exposure to jet fuel. (Original Article)." Occupational and Environmental Medicine 60.12 (December 2003): 969(8) and in Chao, Y, E., Kupper, L. L., Serdar, B., Egeghy, P., Rappaport, S. M., Nylander-French, L. A., "Dermal exposure to Jet Fuel JP-8 significantly contributes to the production of urinary naphthols in fuel-cell maintenance workers", Environmental Health Perspectives, v 114, no 2, p 182-185 (2006). These deleterious effects from naphthalene have warranted closer monitoring to determine the daily exposure of individuals such that better methods to reduce exposure can be created. Although permissible exposure limits (PEL) for JP-8 are presently set at 350 mg/m$^3$, recent studies have shown alterations in lung tissue with as little as 46 mg/m$^3$.

Naphthalene is traditionally measured using typical analytical laboratory techniques such as various forms of gas chromatography, mass spectrometry, FTIR, and laser-induced fluorescence, or by field instruments such as photoionization or flame ionization based detectors. Laboratory techniques have high sensitivity and specificity, whereas present field instruments have very low levels of specificity. Because of the traditional size, weight, and power consumption of laboratory instruments, they are not suitable for significant miniaturization, and present field instruments have inadequate specificity in identifying naphthalene specifically.

A need exists for a method and compact apparatus for distinguishing selected VOCs, whether in a vapor, liquid, or solid state in the environment of interest, and more particularly for a compact, lightweight, portable detection methodology that can accurately assess the presence of such VOCs (e.g. naphthalene) at trace levels.

SUMMARY OF THE INVENTION

It is an object of some embodiments of the invention to provide a compact sensor system for distinguishing one or more selected VOCs while in a vapor state, a solid state, or liquid state.

It is an object of some embodiments of the invention to provide a compact sensor system for distinguishing one or more selected VOCs, while in a vapor, solid, of liquid state, based on detection of native fluorescence stimulated by UV radiation based on one or more of (1) use of rapidly refreshable detection methodology (e.g. new and fresh readings every 5-60 seconds); (2) use of temperature variation elements to cause rapid condensation of VOCs in sample irradiation locations, rapid vaporization of VOCs in sample irradiation locations; (3) use of forced air movement elements to aid in sample location refreshment; (45), use of a small number of discrete spectral bands (e.g. 2-10 bands); (5) use of deep UV wavelengths, e.g. between 185 nm and 300 nm, between 200 nm and 280 nm, or between 220 nm and 250 nm; (6) use of controlled excitation radiation and detection such that detection occurs during excitation while a sample location is at a fixed temperature, is transitioning from a higher to a lower temperature, or is transitioning from a lower to higher temperature, (7) use of controlled excitation radiation and detection such that detection occurs after irradiation is extinguished (e.g. one or more times between 0-100 nanoseconds after extinction of excitation radiation) and while a sample location is at a fixed temperature, is transitioning from a higher to a lower temperature, or is transitioning from a lower to higher temperature, (8) use of data logging and manipulation to provide integrated exposure levels over desired time periods (e.g. hours, work shifts, days, weeks, or the like).

It is an object of some embodiments of the invention to provide a method for distinguishing one or more selected VOCs while in a vapor, solid, or liquid state that can be implemented in a compact system where the system may include a detection chamber or surface or where the system may make use of an existing surface or region, as a detection location, within environment that is being examined.

It is an object of some embodiments of the invention to provide a method for distinguishing one or more selected VOCs, in a vapor, solid, or liquid state, that can be implemented in a compact system based on detecting native fluorescence stimulated by UV radiation based on one or more of (1) use of rapidly refreshable detection methodology (e.g. new and fresh readings every 5-60 seconds); (2) use of temperature variation elements to cause rapid condensation of VOCs in sample irradiation locations, rapid vaporization of VOCs in sample irradiation locations; (3) use of forced air movement elements to aid in sample location refreshment; (4), use of a small number of discrete spectral bands (e.g. 2-10 bands); (5) use of deep UV wavelengths, e.g. between 185 nm and 300 nm, between 200 nm and 280 nm, or between 220 nm and 250 nm; (6) use of controlled excitation radiation and detection such that detection occurs during excitation while a sample location is at a fixed temperature, is transitioning from a higher to a lower temperature, or is transitioning from a lower to higher temperature, (7) use of controlled excitation radiation and detection such that detection occurs after irradiation is extinguished (e.g. one or more times between 0-100 nanoseconds after extinction of excitation radiation) and while a sample location is at a fixed temperature, is transitioning from a higher to a lower temperature, or is transitioning from a lower to higher temperature, (8) use of data logging and manipulation to provide integrated exposure levels over desired time periods (e.g. hours, work shifts, days, weeks, or the like).

It is an object of some embodiments to provide improved detection and analysis methods, devices, or systems for detecting and evaluating organic compounds of interest that may be located on surfaces or within an atmosphere within a sample chamber forming part of a device or as solids, liquids or gases external to the device as detected by exposing the environment around the device to selected excitation radiation and detecting any returning emission radiation (e.g. fluorescence) from the environment to one or more detectors located within the device. The improved methods, devices and systems may provide detection of materials located outside a device housing such as vapors in the atmosphere around the device, solid surfaces within an environment of interest, or even within liquid, paste, slurry, powder, or other flowable or spreadable materials located in the environment of interest. Such surfaces may include, for example, floors, walls, sinks, seats, tables, utensils, tools, surfaces of equipment such as vehicles, food processing equipment, pharmaceutical processing equipment, containers for handling various liquid, paste, or powder materials and particularly if residual amounts of one type of material handled or carried in the containers can contaminate a subsequent material to be handled or carried or where contaminates effecting a first carried or handled material can negatively impact a subsequently handled or carried material. Such materials, that may benefit from improved detection and analysis devices, methods, and systems, may for example include flowable food substances (e.g. milk, yogurt, dough, butter, cheese, fruit juices, peanut butter, and the like), precursor food substances (e.g. bacterial colonies), pharmaceuticals, pharmaceutical precursors, chemical mixtures, water, drinkable liquids, and the like. Other materials include by-products of food, pharmaceutical, and industrial cleaning processes to either ensure completion of removal of desired contaminates or other materials (e.g. by their absence from a waste stream), or to ensure that by-products themselves do not contain dangerous or excessive amounts or concentrations of selected materials.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

In a first aspect of the invention a sensing method for volatile organic compounds includes: (a) providing a sample chamber in which a specific VOC, or combination of VOCs of interest, can enter from the environment and be located at a sample location; (b) varying the temperature of the sample location; (c) providing excitation radiation onto the sample location wherein the excitation radiation has a wavelength in the ultraviolet range and wherein the sample location has a temperature that is different from ambient temperature; (d) receiving native fluorescence emission radiation, from the sample location arising from the excitation radiation, onto at least one optical element which directs the fluorescence radiation along at least one detection path; (e) detecting the native fluorescence emission at at least one location along the detection path; and (f) determining whether the detected native fluorescence corresponds to a VOC.

In a second aspect of the invention a sensing method for volatile organic compounds includes: (a) providing a housing; (b) providing a sample chamber, within the housing, in which a specific VOC, or combination of VOCs of interest, can enter from the environment and be located at a sample location; (c) providing excitation radiation, form a source located within the housing, onto the sample location wherein the excitation radiation has a wavelength in the ultraviolet range; (e) receiving native fluorescence emission radiation, from the sample location arising from the excitation radiation, onto at least one optical element, located within the housing, which directs the fluorescence radiation along at least one detection path, located within the housing; (f) detecting the native fluorescence emission at at least one location along the detection path using a detector located within the housing; and (g) determining whether the detected native fluorescence corresponds to a VOC using an electronic circuit located within the housing; wherein the housing occupies a volume selected from the group consisting of (1) less than 2 liters, (2) less than 1 liter, (3) less than 0.5 liters, (4) less than 0.2 liters; (5) less than 0.1 liters, and (6) less than 0.05 liters.

In a third aspect of the invention a sensing method for volatile organic compounds includes: (a) providing a sample chamber in which a specific VOC, or combination of VOCs of interest, can enter from the environment and be located at a sample location; (b) providing excitation radiation onto the sample location wherein the excitation radiation has a wavelength in the ultraviolet range; (c) receiving native fluorescence emission radiation, from the sample location arising from the excitation radiation, onto at least one optical element which directs the fluorescence radiation along a plurality of detection paths; (d) detecting the native fluorescence emission at a plurality of locations along the detection path using a plurality of detectors; (e) determining whether the detected native fluorescence corresponds to a VOC, wherein the plurality of sensors is selected from the group consisting of between (1) two and one-hundred; (2) two and twenty; (3) two and ten; (4) three and eight; and (5) three and six.

Numerous variations of the first to third aspects of the invention are possible and include, for example, one or more of: (1) the detecting includes detecting in a plurality of discrete spectral bands; (2) the detecting includes at least one detector for each of the discrete spectral bands wherein each detector is located along its own detection path; (3) the determining not only provides an indication of the presence of a VOC of interest but also of a concentration of that VOC in the environment; (4) the determining includes storage of data particular to one or more VOCs of interest and comparing data of detected fluorescence with stored VOC data; (5) the determining further includes comparing the ratios of quantities of radiation detected at two or more wavelengths; (6) producing the excitation radiation using an ultraviolet radiation source that produces an excitation wavelength selected from the group consisting of: (a) less than 350 nm; (b) less than 300 nm; (c) less than 280 nm; (c) less than 250 nm; (e) less than 300 nm but more than 185 nm; (f) less than 300 nm but more than 220 nm; (g) less than 280 nm but more than 185 nm; (h) less than 280 nm but more than 220 nm; (i) less than 250 nm but more than 185 nm; and (j) less than 250 nm but more than 220 nm; (7) the at least one optical element includes a plurality of dichroic filters and wherein the at least one detection path comprises a plurality of detection paths wherein the dichroic filters sequentially segregate the spectral components of native fluorescence emission radiation from the VOC sample into the plurality of detection spectral bands within the sensor; (8) the at least one optical element includes a diffraction grating; (9) the at least one optical element includes a prism; (10) the plurality of spectral bands are selected from the group consisting of: (a) less than 100 spectral bands; (b) less 20 spectral bands; (c) less than 10 spectral bands; (d) less than 7 spectral bands; and (e) less than 4 spectral bands; (10) the step of varying the temperature of the sample location such that variations in VOC concentration occur at the sample location; (11) the tenth variation wherein the varying of the temperature occurs in a repeated cyclic manner with a period selected from group consisting of: (a) greater than ½ second; (b) greater than 1 second; (c) greater than 2 seconds; (d) greater than 5 seconds; (e) greater than 10 seconds; (f) greater than 20 seconds; (g) less than 1 minute; (h) less than 30 seconds; (i) less than 15 seconds; (j) less than 8 seconds; (k) less than 4 seconds, and (l) less than 2 seconds; (12) the tenth variation wherein the step of varying the temperature of the sample location includes lowering the sample location temperature such that concentration of the VOCs at the sample location increases; (13) the twelfth variation wherein the lowering of temperature occurs via use of a thermo-electric device and the temperature is decreased to a value selected from the group consisting of (a) less than 10 degrees C., (b) less than 0 degrees C., (c) less than −10 degrees C., (d) less than −20 degrees C., and (e) less than −30 degrees C.; (14) the twelfth variation wherein detection occurs a plurality of times while the temperature of the sample location is being lowered over a temperature lowering time; (15) the fourteenth variation wherein detection of emission radiation in each spectral band occurs in parallel; (16) the fourteenth variation wherein detection of emission radiation in at least some spectral bands occurs in series; (17) the fifteenth variation wherein the excitation radiation is applied in a series of pulses each having a pulse time; (18) the seventeenth variation wherein a temperature lowering time to pulse time ratio is in a range selected from the group consisting of: (a) greater than 2; (b) greater than 5; (c) greater than 10; (d) greater than 20; (e) greater than 50; and (f) greater than 100; (19) the seventeenth variation wherein at least a portion of the detection occurs during application of excitation radiation; (20) the seventeenth variation wherein at least a portion of the detection occurs between pulses of applied excitation radiation; (21) the tenth variation wherein the step of varying the temperature of the sample location comprises raising the sample location temperature such that concentration of the VOCs at the sample location decreases; (22) the twenty-first variation wherein the raising of temperature occurs in a passive manner; (23) the twenty-second variation wherein the passive manner occurs from shutting off power to a temperature lowing device; (24) the twenty-first variation wherein the raising of temperature occurs in an active manner; (25) the twenty-fourth variation wherein the active manner occurs by applying power to a heating element; (26) the twenty-fifth variation wherein the heating element comprises a thermoelectric device; (27) the twenty-first variation wherein detection occurs a plurality of times while the temperature of the sample location is being lowered over a temperature lowering time; (28) the twenty-seventh variation wherein detection of emission radiation in each spectral band occurs in parallel; (29) the twenty-seventh variation wherein detection of emission radiation in at least some spectral bands occurs in series; (30) the twenty-eighth variation wherein the excitation radiation is applied in a series of pulses each having a pulse time; (31) the thirtieth variation wherein a temperature raising time to pulse time ratio is in a range selected from the group consisting of: (a) greater than 2; (b) greater than 5; (c) greater than 10; (d) greater than 20; (e) greater than 50; and (f) greater than 100; (32) the thirty-first variation wherein at least a portion of the detection occurs during application of excitation radiation; (33) the thirty-first variation wherein at least a portion of the detection occurs between pulses of applied excitation radiation; (34) VOCs in the vapor state at the sample location are detected; (35) the VOCs in a condensed state at the sample location are detected; (36) the method is operated to detect a VOC selected from the group consisting of (a) benzene; (b) toluene; (c) xylene; and (d) naphthalene; (37) providing determination of accumulated exposure of an operator to a VOC of interest; (38) supplying power using a battery; (39) the thirty-eight variation wherein the battery includes a rechargeable battery; (40) communicating information between a portable detector and a base station; (41) the fortieth variation wherein the communicating occurs via one or more of an RF link, an IR link, and a temporarily connected hardwire link; (42) supplying output to a user and taking input from a user; (43) the forty-second variation wherein the supplying output comprises a visual display and taking input comprises a keypad; (44) providing warnings to a user based on VOC detection; (45) the forty-fourth variation wherein warnings are supplied via one or more of a speaker, a buzzer, a vibrator, and a light; (46) the steps of the method are performed by a device which weighs less than two pounds, preferably less than one pound and more preferably less than about 0.75 pounds; (47) the device has a height, a width, and a thickness selected from a group of heights consisting of less than about six inches, more preferably less than about five inches, and even more preferably less than about four inches, a group of widths selected from less than about four inches, more preferably less than about three inches and most preferably less than about two inches, and a group of thicknesses selected from less than about one inch, more preferably less than about 0.8 inches, and more preferably less than about 0.6 inches; (48) use of at least one fan that provides for functionality selected from the group consisting of (a) bringing VOCs into the sample chamber; (b) removing VOCs from the sample chamber; (c) bringing VOCs from the sampling chamber during a cooling down of the sample location; (d) removing VOCs from the sampling chamber during a heating of the sample location; and (49) the providing of excitation radiation includes operating a source selected from the group consisting of (a) a hollow cathode laser; (b) an LED, (c) an LET, (d) a semiconductor laser, (e) and e-beam pumped semiconductor laser.

In a fourth aspect of the invention an analytical instrument for detecting volatile organic compounds (VOCs) includes: (a) a sample chamber in which a specific VOC, or combination of VOCs of interest, can enter from the environment and be located at a sample location; (b) a temperature manipulation element located at the sample location for varying the temperature of the sample location; (c) a source of excitation radiation for providing the excitation radiation onto the sample location wherein the excitation radiation has a wavelength in the ultraviolet range and wherein the sample location has a temperature that is different from ambient temperature; (d) at least one optical element for receiving native fluorescence emission radiation from the sample location arising from the excitation radiation which directs the fluorescence radiation along at least one detection path; (e) a plurality of detectors that detect the native fluorescence emission at at least one location along the detection path; and (f) an electric circuit configured to, or a microprocessor configured or programmed to, determine whether the detected native fluorescence corresponds to a VOC.

In a fifth aspect of the invention an analytical instrument for detecting volatile organic compounds (VOCs) includes: (a) a housing; (b) a sample chamber, within the housing, in which a specific VOC, or combination of VOCs of interest, can enter from the environment and be located at a sample location; (c) a source, within the housing, of excitation radiation, for providing excitation radiation onto the sample location wherein the excitation radiation has a wavelength in the ultraviolet range; (e) one or more optical elements that receive native fluorescence emission radiation, from the sample location that arise from the excitation radiation, which directs the fluorescence radiation along at least one detection path, located within the housing; (f) a plurality of detectors located within the housing that detect the native fluorescence emission at at least one location along the detection path; and (g) an electric circuit configured to, or a microprocessor configured or programmed to, determine whether the detected native fluorescence corresponds to a VOC, wherein the circuit or processor is located within the housing, and wherein the housing occupies a volume selected from the group consisting of (1) less than 2 liters, (2) less than 1 liter, (3) less than 0.5 liters, (4) less than 0.2 liters; (5) less than 0.1 liters, and (6) less than 0.05 liters.

In a sixth aspect of the invention an analytical instrument for detecting volatile organic compounds (VOCs) includes: (a) a sample chamber in which a specific VOC, or combination of VOCs of interest, can enter from the environment and be located at a sample location; (b) a source of excitation radiation that directs the excitation radiation onto the sample location wherein the excitation radiation has a wavelength in the ultraviolet range; (c) at least one optical element that receives native fluorescence emission radiation, from the sample location, which directs the fluorescence radiation along a plurality of detection paths; (d) a plurality of detectors that detect the native fluorescence emission along the detection paths; (e) an electric circuit configured to, or a microprocessor configured or programmed to, determine whether the detected native fluorescence corresponds to a VOC, wherein the plurality of sensors is selected from the group consisting of between (1) two and one-hundred; (2) two and twenty; (3) two and ten; (4) three and eight; and (5) three and six.

In a seventh aspect of the invention a sensing method for an organic compound includes: (a) providing excitation radiation onto a sampling location wherein the excitation radiation has a wavelength in the ultraviolet range and wherein the sampling location holds a sample to be tested in a form selected from the group consisting of vapor, liquid, solid; (b) receiving native fluorescence emission radiation, from the sampling location arising from the excitation radiation, onto at least one optical element which directs the fluorescence radiation along at least one detection path; (e) detecting the native fluorescence emission at at least one location along the detection path; and (f) determining whether the detected native fluorescence corresponds to the organic compound.

In an eighth aspect of the invention a sensing method for organic compounds includes: (a) providing a housing; (b) providing excitation radiation, form a source located within the housing, onto a sample location located outside the housing wherein the excitation radiation has a wavelength in the ultraviolet range; (c) receiving native fluorescence emission radiation, from the sample location arising from the excitation radiation, onto at least one optical element, located within the housing, which directs the fluorescence radiation along at least one detection path, located within the housing; (d) detecting the native fluorescence emission at at least one location along the detection path using a detector located within the housing; and (e) determining whether the detected native fluorescence corresponds to an organic compound of interest using an electronic circuit located within the housing; wherein the housing occupies a volume selected from the group consisting of (1) less than 2 liters, (2) less than 1 liter, (3) less than 0.5 liters, (4) less than 0.2 liters; (5) less than 0.1 liters, and (6) less than 0.05 liters.

In a ninth aspect of the invention a sensing method for organic compounds includes: (a) providing excitation radiation onto the sample location wherein the excitation radiation has a wavelength in the ultraviolet range; (b) receiving native fluorescence emission radiation, from the sample location arising from the excitation radiation, onto at least one optical element which directs the fluorescence radiation along a plurality of detection paths; (c) detecting the native fluorescence emission at a plurality of locations along the detection path using a plurality of detectors; (e) determining whether the detected native fluorescence corresponds to an organic compound of interest, wherein the plurality of sensors is selected from the group consisting of between (1) two and one-hundred; (2) two and twenty; (3) two and ten; (4) three and eight; and (5) three and six.

Numerous variations of the seventh to ninth aspects of the invention are possible and include, for example, one or more of: (1) the detecting includes detecting in a plurality of discrete spectral bands; (2) the detecting includes at least one detector for each of the discrete spectral bands wherein each detector is located along its own detection path; (3) the determining not only provides an indication of the presence of an organic compound of interest but also of a concentration of that organic compound in the environment; (4) the determining includes storage of data particular to one or more organic compounds of interest and comparing data of detected fluorescence with stored organic compound data; (5) the determining further includes comparing the ratios of quantities of radiation detected at two or more wavelengths; (6) producing the excitation radiation using an ultraviolet radiation source that produces an excitation wavelength selected from the group consisting of: (a) less than 350 nm; (b) less than 300 nm; (c) less than 280 nm; (c) less than 250 nm; (e) less than 300 nm but more than 185 nm; (f) less than 300 nm but more than 220 nm; (g) less than 280 nm but more than 185 nm; (h) less than 280 nm but more than 220 nm; (i) less than 250 nm but more than 185 nm; and (j) less than 250 nm but more than 220 nm; (7) the at least one optical element includes a plurality of dichroic filters and wherein the at least one detection path comprises a plurality of detection paths wherein the dichroic filters sequentially segregate the spectral components of native fluorescence emission radiation from the organic compound sample into the plurality of detection spectral bands within the sensor; (8) the at least one optical element includes a diffraction grating; (9) the at least one optical element includes a prism; (10) the plurality of spectral bands are selected from the group consisting of: (a) less than 100 spectral bands; (b) less 20 spectral bands; (c) less than 10 spectral bands; (d) less than 7 spectral bands; and (e) less than 4 spectral bands; (10) varying the temperature of the sample location such that variations in organic compound concentration occur at the sample location; (11) the tenth variation wherein the varying of the temperature occurs in a repeated cyclic manner with a period selected from group consisting of: (a) greater than ½ second; (b) greater than 1 second; (c) greater than 2 seconds; (d) greater than 5 seconds; (e) greater than 10 seconds; (f) greater than 20 seconds; (g) less than 1 minute; (h) less than 30 seconds; (i) less than 15 seconds; (j) less than 8 seconds; (k) less than 4 seconds, and (l) less than 2 seconds; (12) the tenth variation wherein the step of varying the temperature of the sample location includes lowering the sample location temperature such that concentration of the organic compounds at the sample location increases; (13) the twelfth variation wherein the lowering of temperature occurs via use of a thermo-electric device and the temperature is decreased to a value selected from the group consisting of (a) less than 10 degrees C., (b) less than 0 degrees C., (c) less than −10 degrees C., (d) less than −20 degrees C., and (e) less than −30 degrees C.; (14) the twelfth variation wherein detection occurs a plurality of times while the temperature of the sample location is being lowered over a temperature lowering time; (15) the fourteenth variation wherein detection of emission radiation in each spectral band occurs in parallel; (16) the fourteenth variation wherein detection of emission radiation in at least some spectral bands occurs in series; (17) the fifteenth variation wherein the excitation radiation is applied in a series of pulses each having a pulse time; (18) the seventeenth variation wherein a temperature lowering time to pulse time ratio is in a range selected from the group consisting of: (a) greater than 2; (b) greater than 5; (c) greater than 10; (d) greater than 20; (e) greater than 50; and (f) greater than 100; (19) the seventeenth variation wherein at least a portion of the detection occurs during application of excitation radiation; (20) the seventeenth variation wherein at least a portion of the detection occurs between pulses of applied excitation radiation; (21) the tenth variation wherein the step of varying the temperature of the sample location comprises raising the sample location temperature such that a concentration of the organic compounds at the sample location decreases; (22) the twenty-first variation wherein the raising of temperature occurs in a passive manner; (23) the twenty-second variation wherein the passive manner occurs from shutting off power to a temperature lowing device; (24) the twenty-first variation wherein the raising of temperature occurs in an active manner; (25) the twenty-fourth variation wherein the active manner occurs by applying power to a heating element; (26) the twenty-fifth variation wherein the heating element comprises a thermo-electric device; (27) the twenty-first variation wherein detection occurs a plurality of times while the temperature of the sample location is being lowered over a temperature lowering time; (28) the twenty-seventh variation wherein detection of emission radiation in each spectral band occurs in parallel; (29) the twenty-seventh variation wherein detection of emission radiation in at least some spectral bands occurs in series; (30) the twenty-eighth variation wherein the excitation radiation is applied in a series of pulses each having a pulse time; (31) the thirtieth variation wherein a temperature raising time to pulse time ratio is in a range selected from the group consisting of: (a) greater than 2; (b) greater than 5; (c) greater than 10; (d) greater than 20; (e) greater than 50; and (f) greater than 100; (32) the thirty-first variation wherein at least a portion of the detection occurs during application of excitation radiation; (33) the thirty-first variation wherein at least a portion of the detection occurs between pulses of applied excitation radiation; (34) organic compounds in the vapor state at the sample location are detected; (35) the organic compounds in a condensed state at the sample location are detected; (36) the method is operated to detect a organic compound selected from the group consisting of (a) benzene; (b) toluene; (c) xylene; and (d) naphthalene; (37) providing determination of accumulated exposure of an operator to a VOC of interest; (38) supplying power using a battery; (39) the thirty-eight variation wherein the battery includes a rechargeable battery; (40) communicating information between a portable detector and a base station; (41) the fortieth variation wherein the communicating occurs via one or more of an RF link, an IR link, and a temporarily connected hardwire link; (42) supplying output to a user and taking input from a user; (43) the forty-second variation wherein the supplying output comprises a visual display and taking input comprises a keypad; (44) providing warnings to a user based on organic compound detection; (45) the forty-fourth variation wherein warnings are supplied via one or more of a speaker, a buzzer, a vibrator, and a light; (46) the steps of the method are performed by a device which weighs less than two pounds, preferably less than one pound and more preferably less than about 0.75 pounds; (47) the device has a height, a width, and a thickness selected from a group of heights consisting of less than about six inches, more preferably less than about five inches, and even more preferably less than about four inches, a group of widths selected from less than about four inches, more preferably less than about three inches and most preferably less than about two inches, and a group of thicknesses selected from less than about one inch, more preferably less than about 0.8 inches, and more preferably less than about 0.6 inches; (48) use of at least one fan that provides for functionality selected from the group consisting of (a) bringing VOCs into the sample chamber; (b) removing VOCs from the sample chamber; (c) bringing VOCs from the sampling chamber during a cooling down of the sample location; (d) removing VOCs from the sampling chamber during a heating of the sample location; and (49) the providing of excitation radiation includes operating a source selected from the group consisting of (a) a hollow cathode laser; (b) an LED, (c) an LET, (d) a semiconductor laser, (e) and e-beam pumped semiconductor laser.

In a tenth aspect of the invention an analytical instrument for detecting organic compounds includes: (a) a housing; (b) a source, located within the housing, of excitation radiation for providing the excitation radiation onto a sample location selected from the group consisting of (1) within a sampling chamber within the housing and (2) a region external to the housing, wherein the excitation radiation has a wavelength in the ultraviolet range; (c) at least one optical element for receiving native fluorescence emission radiation from the sample location arising from the excitation radiation which directs the fluorescence radiation along at least one detection path; (d) a plurality of detectors that detect the native fluorescence emission at at least one location along the detection path; and (e) an electric circuit configured to, or a microprocessor configured or programmed to, determine whether the detected native fluorescence corresponds to an organic compound.

In an eleventh aspect of the invention an analytical instrument for detecting organic compounds includes: (a) a housing; (b) a source, within the housing, of excitation radiation, for providing excitation radiation onto a sample location wherein the excitation radiation has a wavelength in the ultraviolet range and wherein the sample location has a position selected from the group consisting of (1) within the housing and (2) external to the housing; (c) one or more optical elements that receive native fluorescence emission radiation, from the sample location that arise from the excitation radiation, which directs the fluorescence radiation along at least one detection path, located within the housing; (d) a plurality of detectors located within the housing that detect the native fluorescence emission at at least one location along the detection path; and (e) an electric circuit configured to, or a microprocessor configured or programmed to, determine whether the detected native fluorescence corresponds to an organic compound, wherein the circuit or processor is located within the housing, and wherein the housing occupies a volume selected from the group consisting of (1) less than 2 liters, (2) less than 1 liter, (3) less than 0.5 liters, (4) less than 0.2 liters; (5) less than 0.1 liters, and (6) less than 0.05 liters.

In a sixth aspect of the invention an analytical instrument for detecting organic compounds includes: (a) a source of excitation radiation that directs the excitation radiation onto a sample location wherein the excitation radiation has a wavelength in the ultraviolet range and wherein the sample location has a position selected from the group consisting of (1) within the housing and (2) external to the housing; (b) at least one optical element that receives native fluorescence emission radiation, from the sample location, which directs the fluorescence radiation along a plurality of detection paths; (c) a plurality of detectors that detect the native fluorescence emission along the detection paths; (d) an electric circuit configured to, or a microprocessor configured or programmed to, determine whether the detected native fluorescence corresponds to a VOC, wherein the plurality of sensors is selected from the group consisting of between (1) two and one-hundred; (2) two and twenty; (3) two and ten; (4) three and eight; and (5) three and six.

Numerous variations of the instrument aspects of the invention are possible. Some such variations correspond to the method variations set forth above with steps replaced by appropriate components, circuits, optical elements, and the like.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

DETAILED DESCRIPTION OF PREFERRED EMBODIMENTS

Figure 1A:
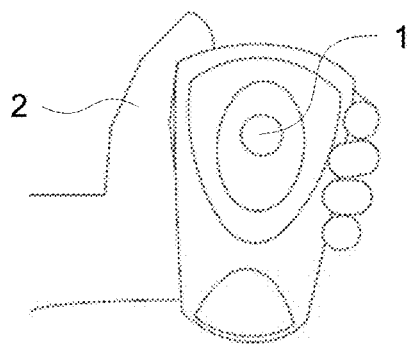
FIG. 1A and FIG. 1B illustrate an example wearable "badge" sensor for naphthalene vapor detection and dosimetry, or other VOC detection and dosimetry, wherein the sensor system can be readily held in a hand or fitted into a vest pocket or carried in some other convenient manner.

Methods and sensor systems of embodiments of the invention based on deep UV (e.g. having a relative narrow band of wavelengths above 185 nm but less than 200 nm, above 200 nm but less than 280 nm, or above 220 nm but less than 250 nm) excited native fluorescence have demonstrated the ability to clearly distinguish between standard jet fuels which contain naphthalene (e.g. MAPLLC Aviation Turbine Fuel Jet A (04posf4658) fuel with about 3% naphthalene compounds) and new, synthetic fuels (e.g. S-8 Synthetic Jet Fuel (06posf5018fuel)) which contains essentially no naphthalene. Various embodiments have demonstrated sufficient sensitivity that trace amounts of naphthalene could be detected in the S-8 jet fuel (without naphthalene) but which was stored in containers where Jet A was previously stored. The embodiments have also demonstrated that naphthalene can be distinguished from other volatile organic compounds (VOCs).

Some embodiments have achieved continuous detection of naphthalene while in the vapor state, without any need for concentration, at low vapor pressure using a miniature deep UV excited native fluorescence detector. Other embodiments provide higher levels of sensitivity using a simple, rapidly refreshable (e.g. in some embodiments this may occur in less than 0.5 second while in other embodiments it may take between 0.5 seconds and 60 seconds or somewhat more, e.g. 2-5 minutes), vapor collector that does not need chemical adsorbents, absorbents, or chelating agents such as molecular imprinted polymers, etc., which typically have problems with level of refreshment, rate of refreshment, and substrate aging.

In some embodiments, the rapidly refreshable vapor collection system and method may employ a simple, miniature, single stage thermo-electric (TE or Peltier) cooler, with a size, for example of about 3 mm×3 mm×1 mm. In one implementation of the method, the TE cooler is cycled periodically from room temperature to about −20 C and back to room temperature. In some alternative embodiments, other low temperature limits may be used. At a sample rate of one cycle per 10 seconds, the power consumption is less than 4 W. In some alternative embodiments, longer or shorter cycling rates may be used. In some alternative embodiments, multiple detections may be made during a single cycle such that presence of different compounds may be further distinguished or verified based on detection of their presence and lack of presence at different temperatures which result from a natural separation that occurs during cold cycling due to condensation differences that result from different molecular weights of their respective molecules at a given temperature. In some alternative embodiments, evaporation rate differences upon heating the sample location may also be used in ascertaining or further verifying the presence or lack of presence of significant quantities of selected VOCs. Naphthalene and other VOCs condense and subsequently freeze on the TE cooler surface where they are excited by UV radiation from a low power deep UV light emitting source (e.g. a diode (LED), a triode (LET), semiconductor laser, or hollow cathode laser) with emission wavelength including at least some wavelengths below for example, about 280 nm. Such deep UV sources are available commercially from Photon Systems and elsewhere. The native fluorescence emissions from the frozen VOCs are detected by a set of photodiodes with dichroic and bandpass filters to select specific spectral marker bands. In the present embodiment, as the TE cooler (i.e. the sample location) is cold cycled, the concentration of naphthalene may be measured approximately every 10 seconds. In some embodiments, an onboard microprocessor deconvolves the spectral data into naphthalene concentration and calculates, records, and stores the instantaneous and/or accumulated naphthalene concentration and may provide audible and visual alarms to the wearer for one or both of instantaneous level and accumulated dose.

In some other alternative embodiments, the current on the TE cooler may be reversed to allow temperatures greater than room temperature to allow removal of the VOCs and/or to allow more rapid cycling at the cost of higher power consumption. In some embodiments, merely turning off the cooler may allow heat from the hot side of the TE device to cause sufficient heating of the sample location to allow a desired cycling rate. In some such embodiments, such passive heating may allow the sample location to be heated to a temperature above ambient temperature. In some embodiments, controlled heating or cooling may be used to give the sample location a desired temperature ramping profile (i.e. minimum temperature, minimum temperature dwell time, maximum temperature, maximum temperature dwell time, transition time/temperature profile, and the like). In some embodiments, one or more forced air devices (e.g. one or more fans that pull air into a sample chamber or force air out of the sample chamber, one or displacement devices, e.g. moving walls, pistons, bellows, expansion chambers, or the like that draw air in or force air out of the sample chamber) may be incorporated into a sensing device.

In some preferred embodiments, the detection system will be provided in the form of a handheld sensor or clothing mountable sensor that a person can carry with them throughout their activities in a region where toxic or other dangerous VOCs may be present. Such VOCs may be present in a work environment based on chemicals that may be present in such an environment due to normal work activities, due to spills, or other accidental releases. In other circumstances such materials may be present from an intentional release for the purpose of causing harm to soldiers and/or civilians in warzones or other areas subject to terrorist attacks.

In some embodiments, VOCs may not be in vapor form in the environment of interest but instead might exist in liquid or solid form on environmental surfaces or containers and detection systems may have openings or windows for directing excitation radiation out of a device housing onto a sampling location or plurality of locations in the environment (e.g. a surface of a piece of equipment, a surface of a liquid, paste, powder, slurry, or the like of interest. Such devices may or may not make use of temperature variations to collect or disperse organic compounds to be evaluated. Such device will have optical elements for seeing or detecting emission radiation coming from the sampling location or locations. Such devices or instruments may use between 1 and N specific wavelength emission bands for detecting and differentiating the materials with the end result being the qualitative determination of the presence of a chemical of interest or the quantification of a concentration or amount of the chemical in question. Different numbers of and different configurations of wavelength bands may be used and are dependent on the requirements of any given test or operational situation. In the pharmaceutical industry, in cleaning validation there are external and internal guidelines for validation of residual "Active Pharmaceutical Ingredients" (API), excipients (better known as fillers) and "Washes" (used to clean the equipment) in or on processing equipment. In many pharmaceutical cases, ingredients of interest may be limited to the API or the API and the Wash concentration as these are the only potentially dangerous contaminants or residuals when moving from one processing operation to a next processing operation. In the food processing arena, there are external and internal guidelines for validation of a more diverse group of chemicals, organics and microorganisms. In many embodiments, excitation radiation will over a range of UV such as 220 nm to 320 nm or some portion thereof while emission (fluorescence) will be evaluated in a different but possibly overlapping range such as 275 nm to 380 nm. The detection methods set forth herein though referring to organic compounds or VOCs may also be used to identify other chemicals as well.

Figure 1B:
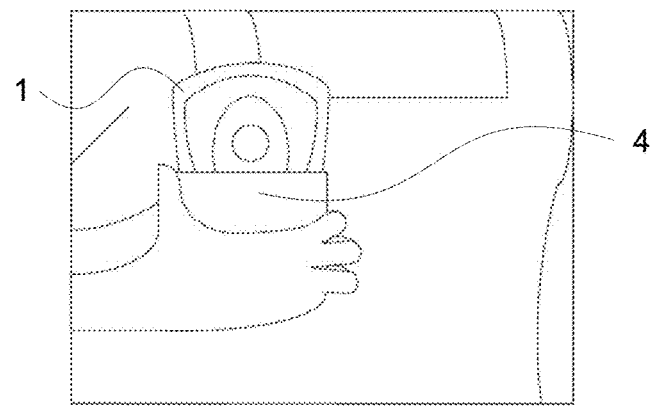

FIG. 1A and FIG. 1B illustrate an example wearable "badge" sensor 1 for naphthalene vapor detection and dosimetry, or other VOC detection and dosimetry, wherein the sensor system can be readily held in a hand 2 or fitted into a vest pocket 4 or carried in some other convenient manner. In some implementations, the device may be preferentially located near the face of a wearer to more accurately provide information concerning the amount of exposure through inhalation that may have occurred. In such embodiments, any release of revaporized VOCs after condensation would preferably be directed away from the face of the user. In some such embodiments, the sensor detection cycles may be correlated to the breathing of the user via appropriate sensors incorporated into the device.

Figure 2:
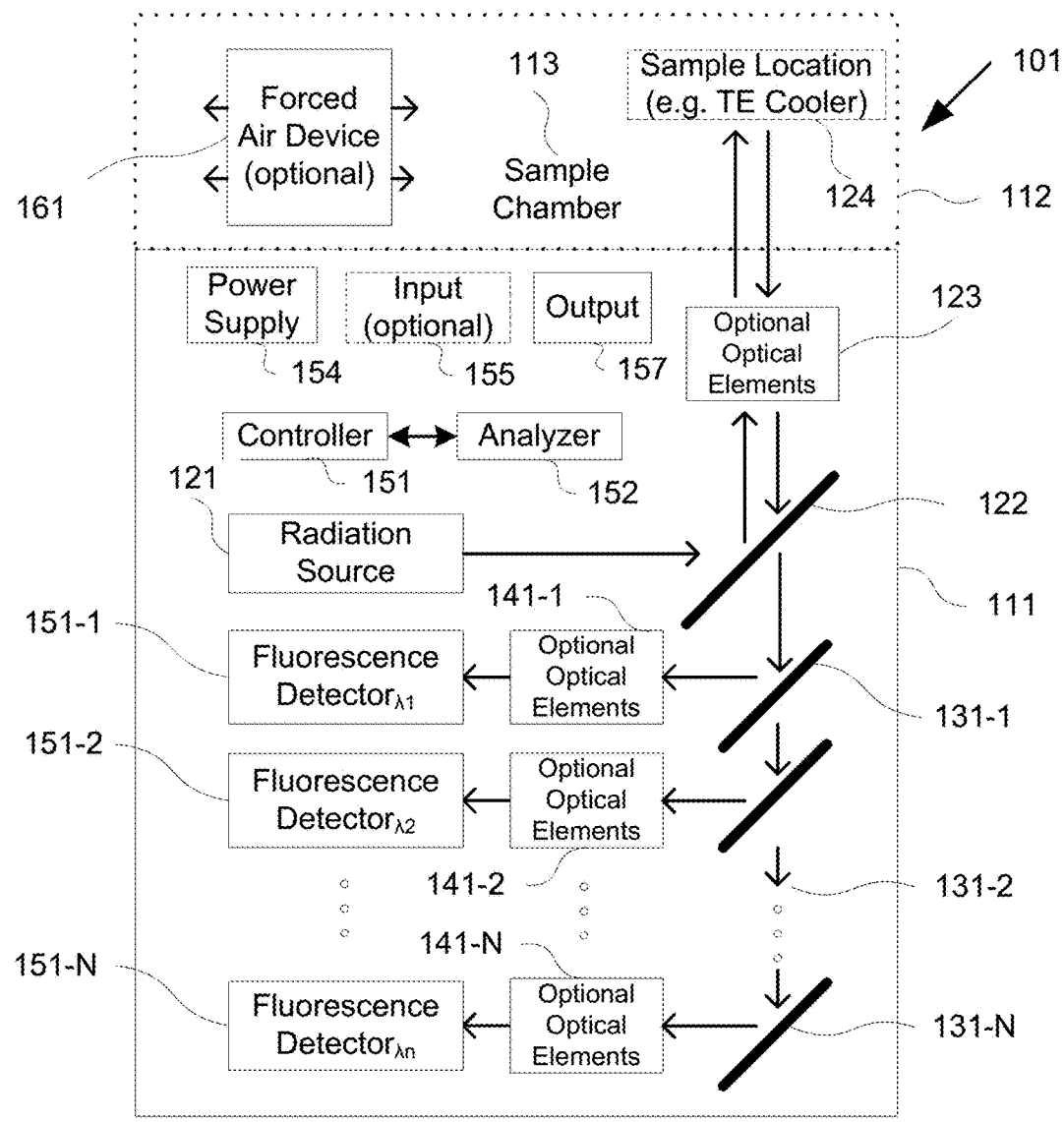
FIG. 2 provides a schematic illustration of a sensor device according to a first embodiment of the invention wherein the device or system may be small and light weight with low power consumption while including a housing with a sealed body portion that holds optical elements and electronic elements and an open portion that surrounds a sample chamber.

FIG. 2 provides a schematic illustration of a sensor device according to a first embodiment of the invention wherein the device or system may be as small as 4"×2"×0.75", or smaller, and have a weight less than 300 g and wherein the device 101 includes a housing 110 that includes a sealed body portion 111 that includes optical elements and electronic elements and an open portion 112 that surrounds a sample chamber 113. The open portion 112 includes a plurality of passages that allow atmospheric vapor including VOCs to enter the sample chamber. The sample chamber may also optionally house one or more forced air devices (e.g. miniature or micro-fans, pistons, bellows or the like) that can aid in forcing air into and out of the sample chamber. The sample chamber also preferably houses an element that helps define a testing or sample location. The element may take the form of a thermo-electric (TE) element that can be used, in conjunction with the power supply 154 and the controller 151, to cause condensation and evaporation of VOCs onto and away from its front surface such that excitation radiation can excite the condensed VOCs which in turn can emit fluorescence radiation along defined paths to a plurality of detectors so that the identity of the VOCs or the presence of selected VOCs, or the lack of presence of selected VOCs can be determined. In some alternative embodiments the sample chamber may also hold additional heating elements that help remove VOCs from the chamber as a whole as required. The sealed portion of the housing may hold various components as further indicated in FIG. 2 such as (1) a power supply 154; (2) an input device 155, such as a key pad, touch screen, switches, capacitive or inductive elements, or the like; (3) an output device, such as a visual screen, an auditory speaker or alarm, a vibrator or other tactile element, (4) a controller 151 such as an ASIC, a microprocessor including memory elements and hard coded or software implemented fixed or selectable sensing, calibration, analysis, uploading, downloading and other functional routines; (5) a source of excitation radiation 121 such as a hollow cathode metal ion laser (such as those set forth in U.S. Pat. No. 6,693,944 which is incorporated herein by reference), an LED, or an LET, or a semiconductor laser or the like (such as those set forth in U.S. Pat. No. 7,590,161 which is incorporated herein by reference); (6) an analyzer 152 which may be part of the controller or a separate component that performs or aids in determining what substances have or have not been detected; (7) one or more optical elements 122 for directing excitation radiation onto the sample location and for passing emission radiation, such elements may include, for example, filters, splitters and the like (in some variations of this embodiment these elements are optional); (8) one or more optional optical elements for shaping the excitation radiation prior to reaching the sample location, (9) one or more optical elements 131-1, 131-2, . . . , and 131-N (such as, for example dichroic filters, diffraction gratings, prisms, or the like) for receiving emission radiation and for directing it along different optical paths for detection by different detector elements; (10) one or more optional optical elements 141-1, 141-2, . . . , and 141-N for filtering and/or shaping emission radiation (e.g. bandpass filters, focusing lenses, and the like) that is being directed along each optical path for each separate spectral detection band; and (11) one or more detectors 151-1, 151-2, . . . , and 151-N (e.g. photodiodes, photomultiplier tubes (PMT), CCD, combinations of such detectors, and arrays of such detectors) for detecting the quantity of emission radiation present along each of the separate spectral detection bands. Various additional elements may be included in a variety of alternative embodiments some of which have been discussed herein above while others will be discussed herein after, while still others will be apparent to those of skill in the art upon review of the teachings herein. In some alternative embodiments, the device may additionally include temperature measuring elements that may be used in feedback loops for controlling the cooling or heating of temperature manipulation elements or which may simply be used to measure temperatures that temperature manipulation elements actually achieve. In other alternative embodiments, the sensor device may include a space (e.g. within the sample chamber) for receiving a porous polymer or other adsorbent filter material that may be used in calibrating the device or for providing a secondary resource that may be used for independent analysis of the environmental VOCs that were encountered. In some embodiments, the number of detectors and associated filters and lens may be less than three (e.g. 1 or 2) while in other embodiments they may number slightly or significantly more than three (e.g. 10 or more). In some alternative embodiments, one or more secondary sources of excitation radiation may be included in device. In some alternative devices the device size may be larger or smaller than that of the most preferred embodiments, may be heavier or lighter than that of the most preferred embodiments, or may use power at a lower rate or higher rate than that of the most preferred embodiments. For example, in some embodiments, the device may have a volume that is up to ½ liters, 1 liter, or even 2 liters or more, it may have a weight up to one pound, up to two pounds, up to five pounds, or even more than ten pounds.

In some embodiments as illustrated in FIGS. 1 and 2, the badge sensor is cell-phone sized with a 300 g weight and 10 hour battery lifetime. The device includes a TE cooler configuration with very low limits of detection, e.g. ~50 µg/m3 or less for naphthalene. In this embodiment, the TE (thermoelectric) cooler consumes the largest amount of energy/power, about 4 J/cycle or 4 W based on a cycle rate of 1 per 10 seconds. The device may use, for example, a 280 nm LED for fluorescence excitation though in other embodiments other sources may be used and in particular sources having shorter wavelengths. The 280 nm LED requires about 100 mJ/s for continuous operation which corresponds to 100 nJ for each microsecond of operation. If operated at 1-100 pulses per second for a 10 second cycle time the power consumption could be on the order of 1 uJ/cycle to 100 uJ/cycle. The photodiodes may operate continuously or only during discrete intervals while the microprocessor will operate continuously and together will require less than about 2 W or 200 mJ/cycle. When power is supplied by a standard lithium-ion battery with an energy density of 460,000 J/kg, the battery weight could be less than about 35 g for a 10 hour battery lifetime per charge. Assuming all of the detection components and a rugged package, the overall weight can be less than 300 g and perhaps as low as 200 g. In some alternative embodiments, the size, weight, and battery lifetime of a continuous detection naphthalene vapor sensor may be smaller, lighter, and longer lifetime, but with a higher limit of detection (i.e. less sensitivity). In still other embodiments, other configurations are possible based on tradeoffs in sensitivity, weight, cycle time, and the like.

In some preferred embodiments, the overall system architecture includes one or more wearable sensor devices or badges (e.g. by different users) and a base unit. In some embodiments, the badge may include a porous polymer adsorbent accumulator which can be tested at a base station or via independent methods for accumulated exposure determination and/or system calibration and verification. In some embodiments, some purposes of a base station may include one or more of (1) reception of and recordation of data from the badge sensors (e.g. via hardwire connection, IR connection, or RF connection with storage to a central computer, e.g. for tracking exposure by individual personnel to selected VOCs, and (2) recharging of rechargeable batteries if they are being used, (3) reprogramming of badges with updated operational routines, and (4) downloading of new calibration parameters. In some embodiments, the base station may also provide sensor calibration and testing capability as well. In some alternative embodiments, the fluorescent detection methods may be supplemented by Raleigh, Raman, or phosphorescence methods. These additional methods may, for example, provide for further identification or confirmation of prior identification of selected VOCs or quantities of VOCs.

These embodiments provide optical-based spectroscopic techniques that are effective, highly miniaturizable, non-contact, non-invasive, methods of detecting and identifying naphthalene and other hazardous volatile organic compounds (VOCs) without the need for sample handling, preparation or use of reagents or other consumables.

Rayleigh, Raman, luminescence, fluorescence and phosphorescence emissions provide an enormous range of optical information about the chemistry of a target sample. Native fluorescence alone also can provide a high level of specificity along with a high level of sensitivity. Naphthalene absorbs strongly in the deep UV, corresponding to its first electronic state, and emits fluorescence associated with the 2-benzene ring structure at longer wavelengths with exceptionally high quantum efficiency. Detection of native fluorescence emissions from naphthalene is the most sensitive method of detection. In condensed phase detection limits of less than 1 femtomole is expected and possibly as low as 1 attomole. In some embodiments, e.g. where chemicals or organic compounds other than naphthalene are of interest, other emissions may be detected and used to help distinguish or quantify the compounds that are present.

When excited at an appropriate wavelength, naphthalene provides a spectral signature that gives excellent identification of the presence of the material. Other materials also have native fluorescence characteristics. However, in the design of the wearable badge being developed here, the only materials entering the detection region of the badge sensor are VOCs and not other potential background interferants. When the excitation and emission wavebands are carefully chosen, naphthalene can be discriminated against other VOCs with high reliability. It is a common notion that excitation at shorter wavelengths causes more interference from background materials. This is incorrect since each material has a unique fingerprint with the fluorescence cross-section and subsequent emission intensity dependent on both excitation and emission (detection) wavelengths. Native fluorescence is independent of excitation wavelength. However, the quantum efficiency with which excitation photons are converted to fluorescence photons is a strong function of wavelength. If excitation or observation wavelengths are not chosen carefully, no chemical information is possible, but if chosen well, high levels of chemical specificity are possible. Asher (S. A. Asher, C. R. Johnson, "Raman Spectroscopy of a Coal Liquid Shows That Fluorescence Interference Is Minimized with Ultraviolet Excitation", Science, 225, 311-313, 20 Jul. 1984) has showed that the range of emission wavelengths due to these processes is almost always limited to wavelengths above about 260 nm. Very few materials fluoresce or phosphoresce below this wavelength, independent of excitation wavelength.

We have previously shown that the chemical identity of a wide range of compounds and background materials can be distinguished effectively with excitation in the deep UV at wavelengths below about 250 nm using native fluorescence alone. (see W. H. Hug, R. Bhartia, A. Tsapin, A. L. Lane, P. G. Conrad, K. Sigapati, and R. D. Reid, "Status of Miniature Integrated UV Resonance Fluorescence and Raman Sensors for Detection and Identification of Biochemical Warfare Agents", Proc. SPIE, Vol. 5994, p 5884J1-12, Boston, Mass. October 2005 and R. Bhartia, W. F. Hug, E. C. Salas, K. Sijapati, A. L. Lane, R. D. Reid and P. G. Conrad, "Biochemical detection and identification false alarm rate: dependence on wavelength using laser induced native fluorescence", Proc. SPIE, Vol. 6218, Orlando, Fla. April 2006). Each of these papers is incorporated herein by reference as if set forth in full.

Figure 3:
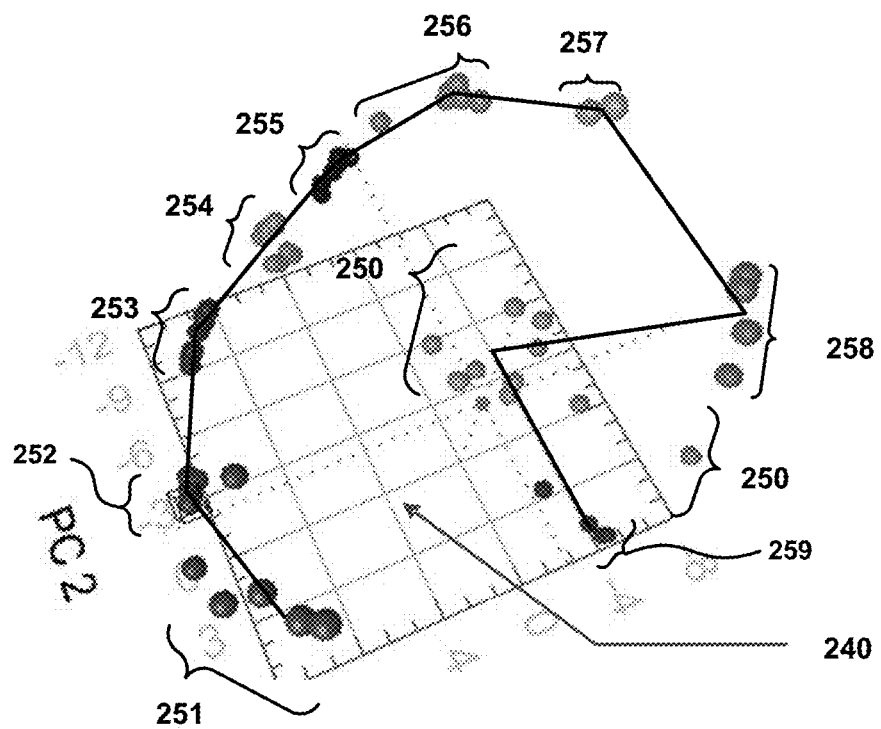
FIG. 3 illustrates the separation of different VOCs when using an excitation wavelength of 235 nm in 3D chemometric space.

FIG. 3 illustrates the separation of different VOCs when using an excitation wavelength of 235 nm. The 3D coordinate "space" in which this figure is illustrated is a "chemometric" space 240 using cluster analysis on a multivariate technique, Principal Component Analysis (PCA), to compare excitation-emission-intensity spectra of hundreds of samples arranged in 10 groups of typical targets and background materials. The target groups in FIG. 3 consisted of single ring aromatic compounds such as benzene, aromatic amino acids, and other compounds (251 and 252), bacterial spores (253), vegetative bacterial cells (Gram + and Gram −) with cellular components (254), double ring aromatics including naphthalene (255), nitrogen based hetercycles including (256), 3 ring polyaromatic hydrocarbons (PAHs) (257), quadruple ring PAHs (258), and >5 Ring PAHS (259). A "background" group (250) including pollen, dust, minerals, and household materials (sugar, flour, corn starch, and the like), was shown not to interfere with the target groups.

The specificity of identification can be accomplished using limited number of selected native fluorescence marker bands. Major advantages accrue from using fewer numbers of detection bands including 10× to 50× improvements in signal strength and dramatic improvements in sensor ruggedness and reliability due to reduction in alignment sensitivities, without serious loss of specificity. Many of the materials shown in FIG. 3 above are not relevant to a naphthalene focused dosimeter since they would not be expected to be able to contaminate the interior detection volume within the badge, which will be protected (Pleil, J. D., Smith, L. B., Zelnick, S. D., "Personal exposure to JP-8 jet fuel vapors and exhaust at Air Force Bases", Environmental Health Perspectives, v 108, n 3 p 183-192 (2000)). This referenced article is incorporated herein by reference as if set forth in full herein.

Figure 4A:
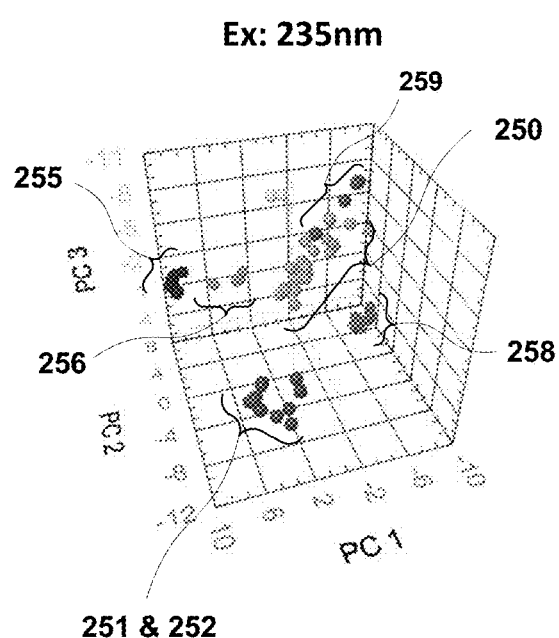
FIGS. 4A and 4B provide plots showing how naphthalene may be differentiated from other materials when 235 nm excitation wavelength radiation is used and when 300 nm excitation wavelength radiation is used respectively.
Figure 4B:
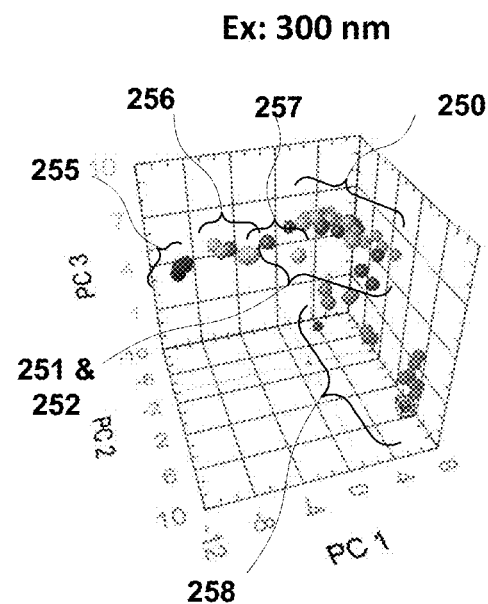
Figure 5:
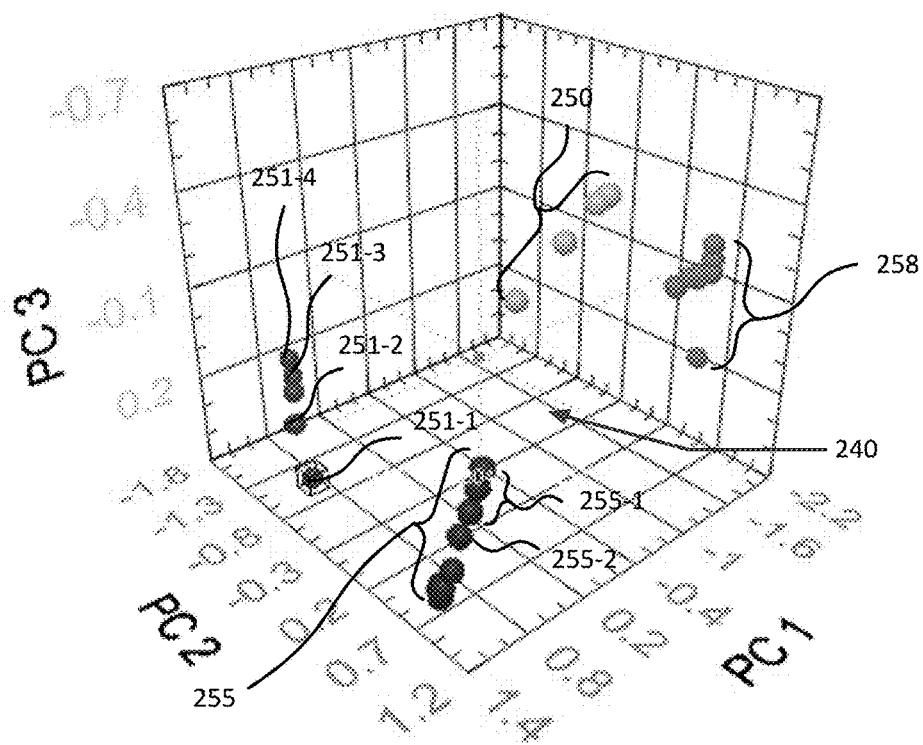
FIG. 5 provides a 3D chemometric plot illustrating the differentiation possible for several volatiles found in jet fuels using only 6 discrete fluorescence bands and a single excitation wavelength at 255 nm FIG. 6 provides a 3D chemometric diagram depicting the locations of various compounds in normalized 3-emission-band space.

Using naphthalene as an example of a material of primary interest, the plots of FIG. 4A, FIG. 4B and FIG. 5 illustrate how this material may be distinguished from other materials. FIGS. 4A and 4B, provide plots in principal component space that respectively show the ability of native fluorescence detection to differentiate naphthalene 255 from a variety of environmental chemicals and background materials using excitation at 235 nm (FIG. 4A) and 300 nm (FIG. 4B). Although excitation at 300 nm provides a clear separation of the naphthalene group 255 from the other organics, it is difficult to distinguish other important hazardous organic compounds such as BTEX (benzene, toluene, ethylbenzene, and xylene,) 251 & 252 since the BTEX materials have positions that are intermixed with other materials. In addition, due to the typical large bandwidth of LED sources at 300 nm, the LED excitation linewidth overlaps naphthalene emission linewidth and the use of filters to separate these bands may cause serious decrease in sensitivity. In some embodiments however, it may be acceptable to use 300 nm excitation using large linewidth LED sources, particularly if appropriate filtering is applied to the excitation radiation prior to its incidence on the target location.

In some preferred embodiments, the incorporation of deep UV excitation and fluorescence detection into a badge-style dosimeter detector, the spectral analyzer needs to be small and it is not practical to incorporate a full spectrometer. Therefore, it is desirable to determine required spectral features that enable a desired level of chemical differentiability while using a limited number of bandpass filters coupled to photodiode detectors. The effect of utilizing six discrete bands along with an excitation wavelength of 255 nm can be seen in the chemometric space of the principal component plot of FIG. 5 wherein components of JP8 are plotted and wherein many of the materials shown in FIG. 3 and FIGS. 4A and 4B have been removed since they do not represent the environment of detection within the enclosed space inside the badge sensor. With this small number of detection bands and limited material exposure range, it is possible to differentiate naphthalenes 255 (dimethyl naphthalene 255-1 and ethyl naphthalene 255-2) from the BTEX and related chemicals 251 and 252 (benzene 251-1, dichlorobenzene 251-2, toluene 251-3, and xylene 251-4) as well as from other organic materials 258 (including 3-ring polycyclic aromatic hydrocarbon molecules such as anthracene) and background materials 250. As indicated, separation within individual groups can be achieved. A list of the constituents of JP8 shows that the most volatile compounds are materials such as heptane, octane, nonane, etc. that do not exhibit native fluorescence. Only three compounds contained in JP8 emit fluorescence and have higher volatility than naphthalene including xylene, 2-ethyltoluene, and mesitylene (Gregg, S. D., J. L. Campbell, J. W. Fisher, and M. G. Bartlett, "Methods for characterization of Jet Propellant-8: vapor and aerosol", Biomed. Chromatograph. 21, pp. 463-472, March 2007). And these compounds have uniquely distinguishable native fluorescence emission spectra.

The data in FIGS. 3-5 were obtained on pure materials using a Hitachi F4500 spectrofluorimeter.

Figure 6:
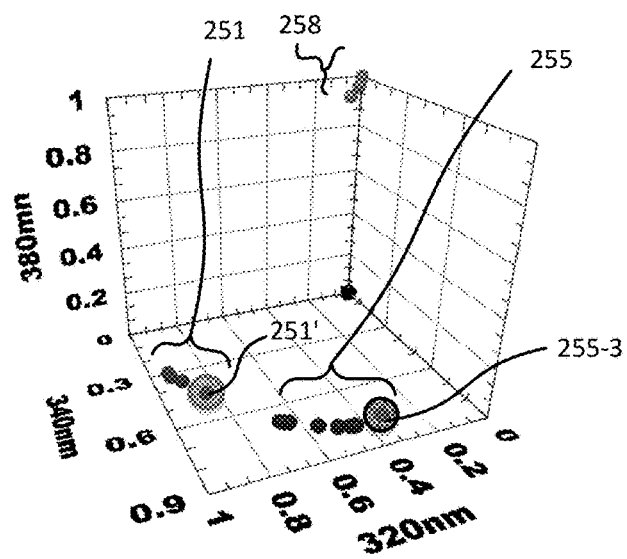

Because spectral complexity associated with naphthalene detection in the badge sensor is relatively simple, a simpler and faster method of chemical identification is possible (i.e. faster and simpler than principle component analysis (PCA) as illustrated in FIGS. 3-5). FIG. 6 provides a plot of various compounds in normalized three-dimensional emission band space (i.e. based on use of three emissions bands, including a 320 nm band, a 340 nm band, and a 380 nm band). In this plot various forms of naphthalene 255 are found at various concentrations including as found in Jet A fuel 255-3. The spheres 251 are single ring organic molecules such as benzene, toluene, xylene (i.e. BTEX 251) including as found in S8 jet fuel251'. The spheres 258 in the upper most portion of FIG. 6 are indicative of various 3-ring polycyclic aromatic hydrocarbon molecules such as anthracene. The results in FIG. 6 employ an excitation wavelength at 280 nm.

To determine the ability to differentiate naphthalene and naphthalene bearing fuel vapors at different wavelengths, we developed a parameter called the Specific Differentiability Factor, SDF, which is described in detail in a recent Applied Spectroscopy paper by Bhartia, Hug, et al. who are inventors on this application (see R. Bhartia, W. F. Hug, E. C. Salas, R. D. Reid, K. K. Sijapati, A. Tsapin, W. Abbey, P. G. Conrad, K. H. Nealson and A. L. Lane, "Classification of Organic and Biological materials with Deep UV Excitation", Applied Spectroscopy, Vol. 62, No. 10, October 2008). This referenced paper is hereby incorporated herein by reference as if set forth in full herein. SDF measures the scalar distance in the three dimensional space illustrated in FIG. 6 between the naphthalene-bearing chemicals and any other compound, whether a single ring, 3-ring or other polycyclic aromatic hydrocarbon. These results are shown below in FIG. 7, where the specific differentiability factor (SDF) for naphthalene compounds is shown versus excitation wavelength for confidence intervals at 2, 3, and 4 standard deviations labeled with reference numbers 302, 303, and 304.

Figure 7:
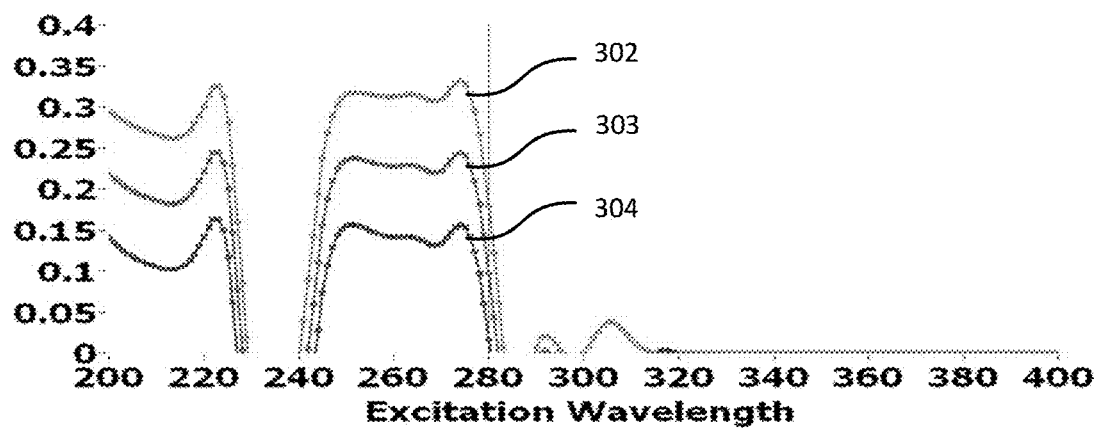
FIG. 7 provides a plot of Specific Differentiability Factor (SDF) for naphthalene compounds versus excitation wavelength.
Figure 8:
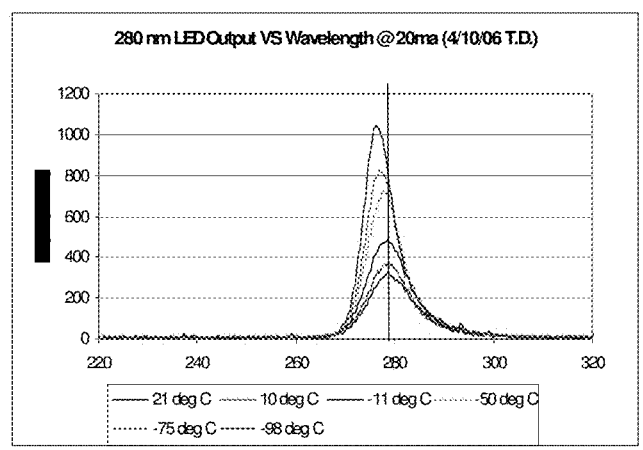
FIG. 8 provides a plot of emission spectra for Photon Systems 280 nm LED (Model PSI UVLED280).

The ideal excitation and observation wavelength or wavelengths depends on the specific goals of the sensor system. For example, if only naphthalene vapors are of interest, certain tradeoffs may be available while for other materials or material combinations, other constraints and tradeoffs may exist. In view of the teachings herein it is within the ability of those of skill in the art to make a selection between these tradeoffs. In some embodiments a 280 nm LED may be used since the output power is higher and lifetime is longer for these LEDs compared to LEDs at shorter wavelengths; however, in other embodiments shorter or longer wavelength LEDs may be used. The bandwidth of 280 nm LEDs is quite large, as shown in FIG. 8 for Photon Systems Model UVLED280 covering a spectral region down to about 270 nm where a high level of naphthalene differentiability is possible as seen in FIG. 7. Further optimization of the LED choices, other radiation source choices, and other excitation wavelength choices (e.g. excitation wavelength filtering) are possible.

Figure 10:
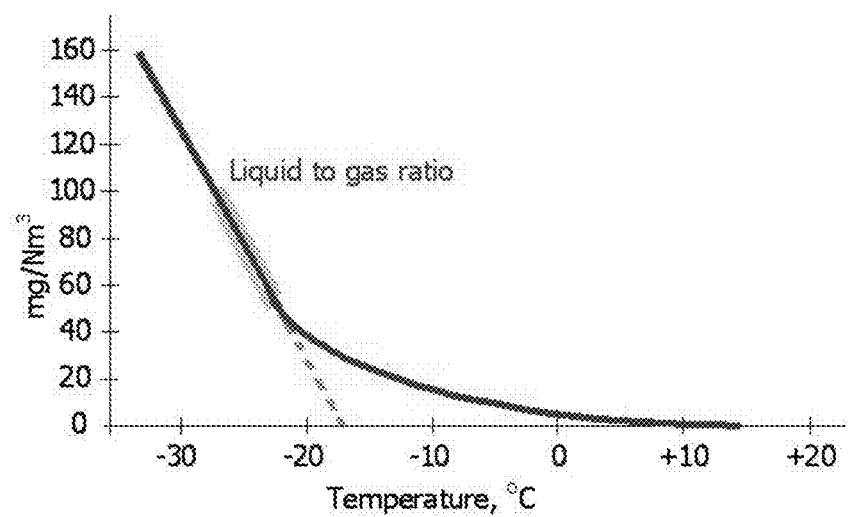
FIG. 10 provides a plot of liquid to gas ratio versus cold finger temperature where N in the units displayed on y-axis refers to standard temperature and pressure.

A comparison of FIGS. 7 and 8 illustrate the overlap of the SDF spectra and the emission spectra of 280 nm LEDs, although there is variability from LED to LED in the output spectra. The plot of FIG. 6 was created based on three native fluorescence emission bands centered at 320 nm, 340 nm, and 380 nm, respectively. Different results would occur for a different sets of detection wavelengths, but this set seems to be effective for detecting and discriminating naphthalene. Any of several methods may be used to select regions of the space in FIG. 10 related to naphthalene or no-naphthalene detection. These methods include, for example, support vector machines.

Figure 9:
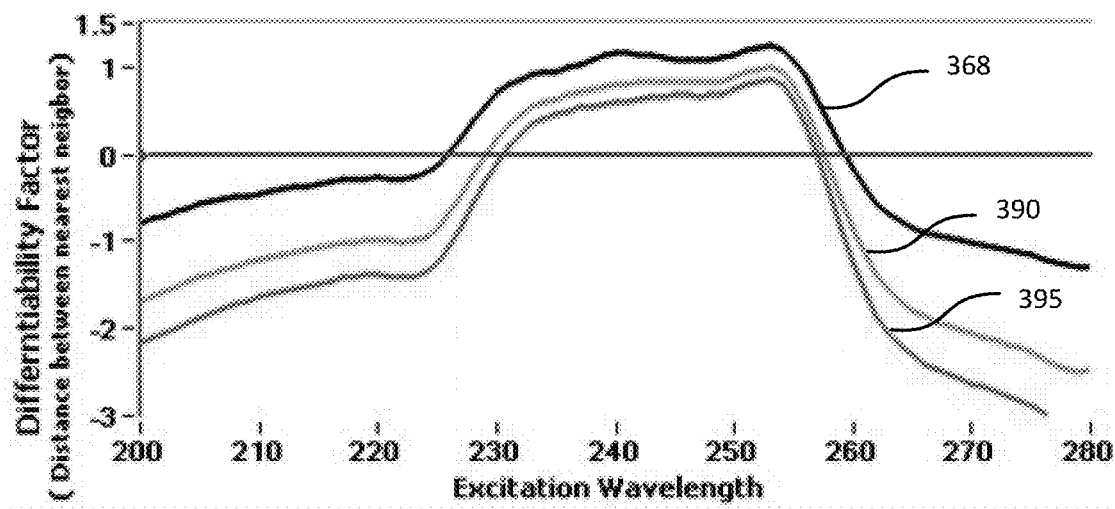
FIG. 9 shows the Overall Differentiability Factor, ODF as a function of excitation wavelength using six detection bands.

In other embodiments, the sensor systems and methods may be extended from naphthalene to other hazardous VOCs such as benzene, toluene, xylene, etc. FIG. 9 shows the Overall Differentiability Factor, ODF (which is also described in the Bhartia/Hug Applied Spectroscopy publication reference above) as a function of excitation wavelength using six detection bands.

The Overall Differentiability Factor is a measure of the minimum distance, in chemometric space, between two groups or classes of chemical compounds. FIG. 9 is the ODF for the range of chemicals shown in FIG. 5, the VOCs expected to be encountered for exposure to jet fuels. Values equal to or greater than zero indicate that the separation between groups in chemometric space is greater than 3 sigma. The individual lines labeled with reference numbers 395, 390, and 368 show confidence levels at the 95%, 90%, and 68.3% levels. This shows that the optimum excitation wavelength to differentiate this wider range of VOCs is deeper in the UV. Light emitting triodes may be useful as such sources. For example, ideal excitation wavelength for differentiating BTEX, naphthalene, and anthracine is in the deep UV between 230 nm and 260 nm.

Different embodiments of the invention may involve different methods for collecting vapor for detection and identification. As noted above one method may be based on the direct measurement of native fluorescence emission in selected spectral "marker" bands from a mixture of volatile organic compounds (VOCs) as they condense and freeze on a temperature cycled "cold finger" or sample location within the badge, and then relating these detected emissions to both chemical identity of the vapor and its concentration. In a preferred embodiment, a small thermoelectric (TE) device is contained in the wearable badge. For example, the temperature of the small (e.g. 6 mm$^2$) "cold finger" head of the TE device may be cycled between hot and cold with a time constant of 10 seconds. At 10 seconds per cycle the TE cooler power consumption is about 4 W. In other embodiments other time constants may be used?

In some embodiments, a detection cycle begins when the TE device is heated to drive off any residual condensed material on its surface and prepare the detection surface for a "new" measurement. Then the TE device cools to a low temperature, perhaps minus 40° C. During this cooling cycle condensable vapors in the atmosphere around the device begin to condense and freeze on the cold surface. Since the cold surface is small and of low thermal mass the temperature cycling can be rapid without significant power consumption. In some embodiments, micro-fans or other air forcing devices may be used to help remove re-vaporized VOCs prior to initiating a next cool down cycle.

As condensation occurs, the heaviest compounds of the vapor mixture condense first followed by the lighter compounds in descending order of molecular weight. Unlike the water dew point which occurs at a specific temperature for a given atmospheric pressure and water vapor content in the atmosphere, jet fuel vapors are a mixture of many components, each of which has a distinct dew point temperature, condensation occurs gradually across a range of temperatures. As the vapor pressure of a compound increases, so does its dew point. Therefore, for a given cold finger temperature, the rate of condensation on the cold finger, and the amount collected in a fixed time, depends on concentration of the component compound.

In the natural gas "industry" the range of dew point is expressed in the liquid to gas ratio (LGR) curve (FIG. 10), which shows the region referred to commonly as the 'hydrocarbon tail', which demonstrates this phenomenon. This shows that the theoretical dew point (defined as the temperature at which the first of the heaviest end components bond together from gaseous to liquid phase) would be some 20° C. or more higher than the measurable dew point where the first visible, and thus, detectable formations of condensates will occur.

In the case of the naphthalene badge sensor of some of the embodiments herein, the naphthalene will condense later in the cooling cycle than various parafins and other organic molecules with higher molecular weight. As the temperature of the cold finger is reduced, VOCs in the air surrounding the badge begin to collect on the cold finger while being irradiated with deep UV radiation from a deep UV LED, LET, or laser emitting, e.g., between 220 nm and 300 nm. Fluorescence emission is monitored in several spectral bands from (e.g. from 280 nm to 400 nm). The spectra are continuously converted to chemical identity and concentration with an onboard microprocessor so the chemical nature of the condensate and its concentration is recorded as a function of time during both heating and cooling portions of the measurement cycle. In some embodiments, the excitation radiation sources may be operated continuously or may be pulsed on and off, e.g. to save energy or to allow detection to occur during build up and decay periods. In some embodiments single detections may be made during each cycle while in other embodiments multiple detections may be made during each cycle as discussed herein before (e.g. 1-20 detections per second during cool down and or during heating). The onboard microprocessor continuously logs the data and may determine an accumulated dose as well as a current exposure. In some embodiments, data logging may occur in the badge sensor itself while exposure calculations may be made by a base or docking station.

Figure 11:
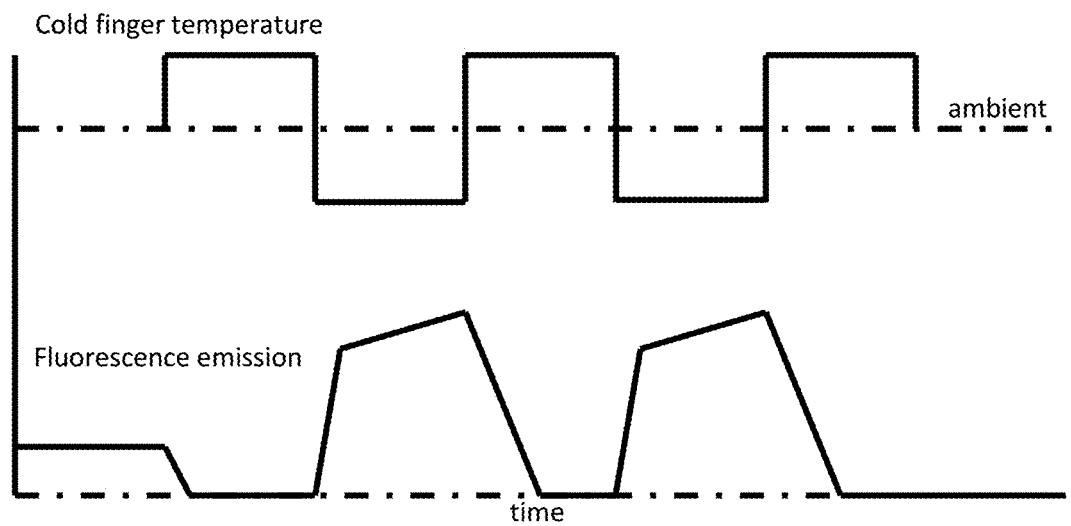
FIG. 11 provides a schematic plot comparing cold finger temperature and native fluorescence emission versus time FIG. 12 provides a schematic diagram showing the relationship between some components in an example wearable badge sensor using a single detector.

As illustrated in FIG. 11, a heating cycle proceeds a cooling cycle to eliminate any residue on the cold finger from a prior cycle. In some embodiments, at the end of the heating cycle the fluorescence emissions from the sample location or cold finger form the baseline from which any changes are measured during the cold, condensation, portion of the cycle or to which comparisons are made for data logged during the heating portion of the cycle. As noted above, in some embodiments, a fan or other forced air device may be used during or between cycles to bring gas in or to remove gas from sample chamber. In some embodiments heating may occur passively (e.g. by warming of the cold finger due to heat flow from a hot side of a TE device or simply by the existence of a surrounding higher ambient temperature (while in other embodiments heating may occur actively (e.g. by reversing the polarity of electrical supply to a TE device).

One of the operating parameters of the badge sensor system is the cooling rate of the TE device. If the cooling rate is too slow the cold finger surface will "flood" with high-end hydrocarbons before the lower end, naphthalene condenses. Faster cooling is better since the entire range of compounds will condense together at a rate in proportion to their partial pressure. However, even with fast cooling of the cold finger, there may come a time after which the cold finger "floods" and the jet fuel or other condensing VOC materials begin to "drip" off of the cold finger. This time constant will depend on overall vapor density of the VOC mixture and the temperature of the cold finger.

Figure 12:
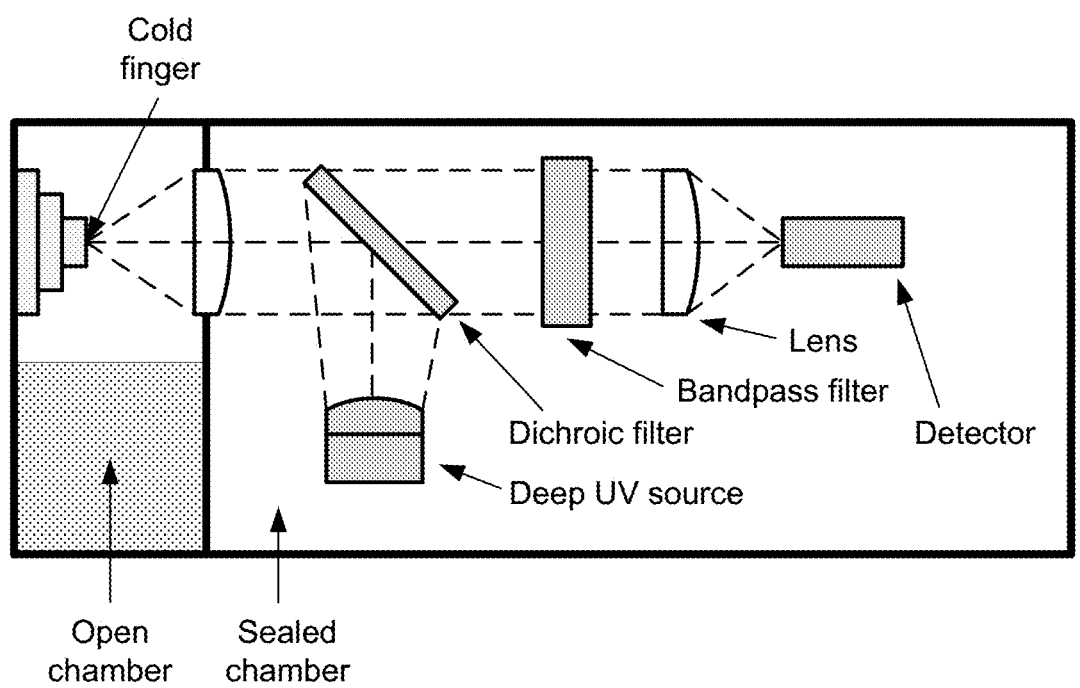

The temperature cycling and measurements discussed above may be made on a multi-detector embodiment such as that shown in FIG. 2 or on a single detector (e.g. a photodiode or PMT) embodiment such as that shown in FIG. 12. In an alternative to the embodiment of FIG. 12, the band pass filter may be replaced by beam spreading device (e.g. a diffraction grating or a prism) and the detector may be replaced by a detector array (e.g. a CCD array, a photodiode array, a PMT array) such that in effect multiple detectors are provided and multiple spectral bands can be utilized in the analysis process. Numerous variations of the components of this embodiment are possible and are similar to those for the embodiment of FIG. 2 as discussed above.

In still other embodiments of the invention there may be no collection of vapor but instead a direct reading of materials on a surface of interest while those materials are in a solid, liquid, or semi-liquid form. In still other embodiments the surface of interest may be in liquid or semi-liquid form such as a container of mixing pharmaceutical components or food components wherein the instrument is not looking for surface residuals but instead looking for contaminates in the mixture or even trace amounts of intended ingredients in the mixture.

In situations where, the dominant use of the badge sensor is to monitor and protect users in fueling environments, it is only necessary to focus calibration efforts on detecting naphthalene concentration, for example, in the atmosphere surrounding the fueling operator to determine the hazard this person is under. Assuming the sensor is configured with excitation radiation at 280 nm, and detection in three bands at 320 nm, 340 nm, and 380 nm, the sensor will clearly identify the presence of naphthalene-bearing jet fuels, per FIG. 6. As the cold finger in the sensor is cycled from hot to cold, as illustrated in FIG. 11, fuel vapor begins to condense and a chemometric signature begins to form as the condensation reaches detectable levels. The concentration of naphthalene may be determined by the amplitude of the native fluorescence signature detected at the end of the cold cycle, before the cold finger temperature is cycled to hot. The values achieved will depend on the duration of the cold cycle, therefore the cold cycle must first be established to a point where sensor "flooding" does not occur under any level of ambient concentration, as described earlier. The sensor must then be calibrated to achieve the ability to determine absolute naphthalene exposure values.

In some embodiments, identification of the presence of naphthalene, or other VOC of interest, may be determined using normalized spectra where the signal in each of the three bands is divided by the sum of signals in all bands. In the case of naphthalene or other fuel component VOCs of interest, the absolute fuel vapor density is determined by the sum of signals in all bands. Various calibration methods are possible and will be understood by those of skill in the art. As an example, a straight forward calibration method may include use of a fuel with a known concentration of naphthalene, or other VOC of interest, which may be exposed to the sensor at various total vapor pressures (of all fuel components). The known concentration is divided by the sum of the signals in all detection bands measured at the end of the cold cycle to create a detection constant for concentration. Linearity of the sensor can also be measured and a look-up-table inserted into the sensor to determine concentration versus signal level. The measurement is for all VOC components, but the amount for naphthalene is determined from the known concentration of naphthalene in the fuel. In some embodiments, it may be assumed that the maximum naphthalene fraction will be 3% and the naphthalene concentration may be computed based on this assumption, which would result in the computed concentration of naphthalene will be a maximum value and any fuel mixture with lower levels of naphthalene will result in an overestimate in the conservative direction.

Figure 13:
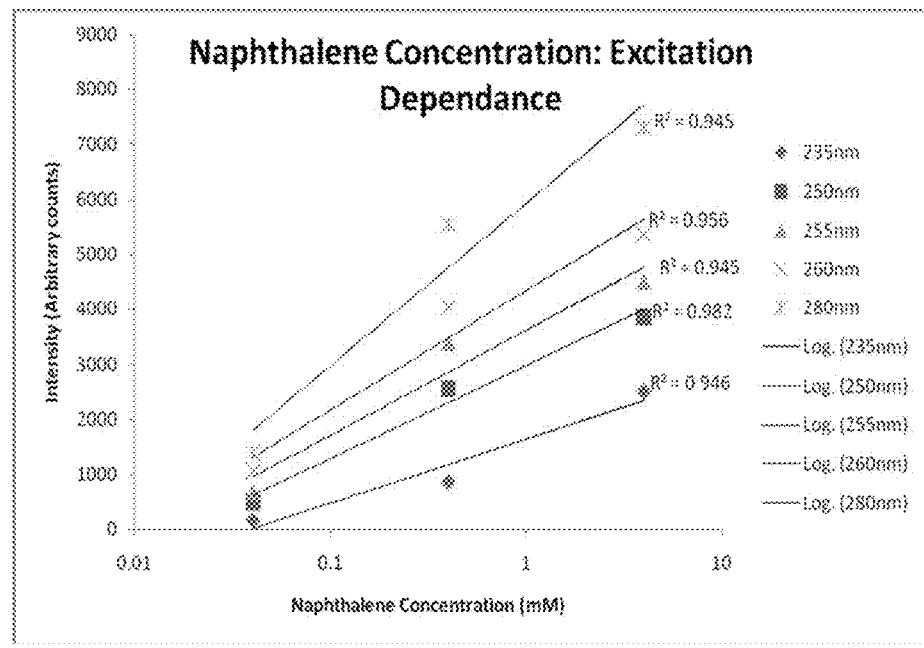
FIG. 13 provides a plot of excitation dependence in arbitrary units on naphthalene concentration linearity (semi-log plot).
Figure 14:
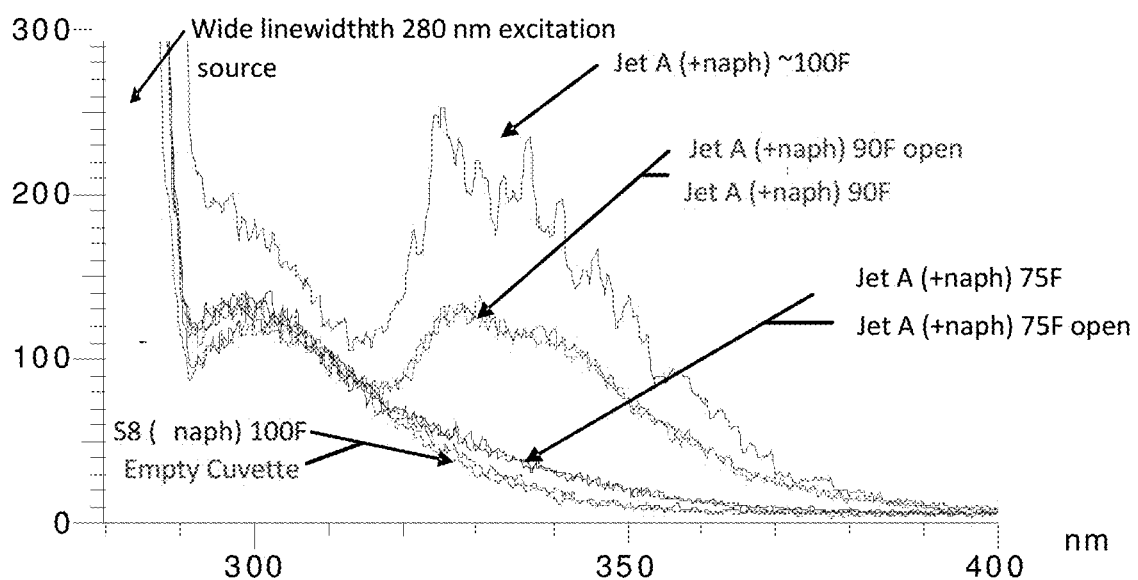
FIG. 14 provides a plot of native fluorescence spectra of gas-phase jet fuels: Jet A (containing naphthalene) and S8 (not containing naphthalene) with excitation at 280 nm.
Figure 15:
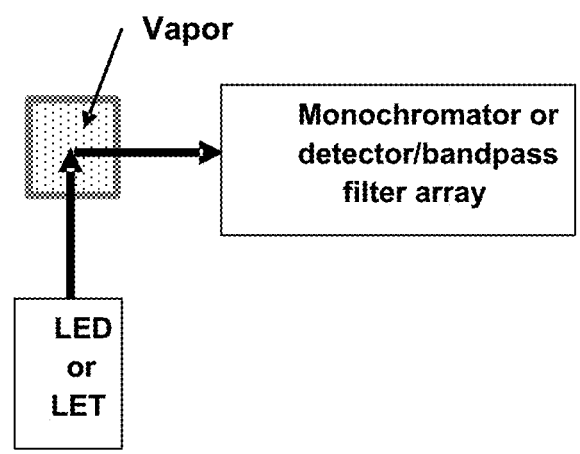
FIG. 15 provides a schematic of direct vapor-phase naphthalene detection device or other VOC detection device.

A more refined, naphthalene-only measurement may use only the 337 nm band since this is the signature band for naphthalene and is shown in FIG. 14. FIG. 14 provides a plot of relative intensity of native fluorescence spectra of various gas-phase jet fuels, Jet A (containing naphthalene) and S8 (not containing naphthalene) with excitation at 280 nm. (Jet A is known to contain naphthalene at ~1.8 wt % and S8 is presumed to NOT have a detectable amount.). These data were taken using a Hitachi F4500 spectrofluorimeter and represents detection values which are not very sensitive, owing to the use of a low source radiance xenon arc lamp and high detection losses in this instrument. However, these determinations are believed to be conservative estimates of what is possible in a wearable badge. The concentration of naphthalene was ranged from 0.04 mM to 4 mM and was run at excitation wavelengths from 200-400 nm. The equivalent of 57 μg/m3 in the condensed phase and 1 g/m3 in the vapor phase were measured. FIG. 13 shows the logarithmic relationship between fluorescence intensity and concentration in this concentration range for excitation wavelengths that are available from LEDs or LETs. At 280 nm, a factor of ten change in concentration of naphthalene leads to a factor of two change in fluorescence emission. In this range of concentration, excitation at or around 280 nm is optimal however other wavelengths of excitation also show a log-linear relationship In some alternative badge sensor embodiments, it is believed possible to remove the TE cooling and heating device from the system and make direct measurement of naphthalene, and possibly other VOCs, while in the vapor state. Some results have indicated that it is possible to clearly detect and identify naphthalene in the gaseous or vapor state using a low radiance arc lamp, equivalent to the emission from a light emitting diode. The data in FIG. 14 are for jet fuel vapor pressures in equilibrium at temperatures ranging from about 75° F. to 100° F. The data in FIG. 21 were obtained using a Hitachi F4500 spectrofluorimeter with excitation wavelength set at 280 nm and bandwidth of 5 nm. A small volume (~10 ul) of Jet A with naphthalene or S8 without naphthalene was deposited at the bottom of a fused silica cuvette, which was inserted into the spectrofluorimeter. A cap was placed on the top of the cuvette to capture the fuel in the cuvette volume. Very rapidly the fuel vapor pressure came into equilibrium at the cuvette temperature and the spectral signatures were stable. FIG. 14 shows the emission spectrum for an empty cuvette, a cuvette with S8 sample at room temperature, and a cuvette with Jet A at room temperature (75° F.), at 90° F., and 100° F. Even at 75° F. the signature of naphthalene in the 320 nm to 360 nm range is detectable. The optical arrangement of this type of embodiment is shown below in FIG. 15. The radiation source was a xenon arc lamp for the data in FIG. 14 but could be an LED or LET in a final sensor or even a plurality of LEDs or LETs.

In some embodiments the photodetectors in the badge sensor system will be photodiode detectors with a quantum efficiency at about 60%.

Each paper or patent referenced herein above is hereby incorporated herein by reference as if set forth in full herein.

It should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference. For example, the teachings set forth in U.S. Pat. No. 8,395,770, previously incorporated herein by reference, provide a number of different steps, methods, components, and component configurations that can be used in combination with the specific methods and devices set forth above or can be used in the alternative to some of the steps or components set forth above. For example, FIGS. 6A-6F of the '770 patent present method embodiments that may be used to implement fluorescence only detection methods as set forth herein or a combination of fluorescence and other emission detection methods. The same is true for the embodiments of FIGS. 7A-7B, FIGS. 8A-8C, FIGS. 9A-9C, FIGS. 10A-10C, and FIGS. 11A-11B of the '770 patent. Modifications to the other embodiments of the '770 patent can also provide fluorand 8Bethod of the All possible variations of these components are intended to be herein contemplated.

It is intended that the aspects of the invention set forth herein represent independent invention descriptions which Applicant contemplates as full and complete invention descriptions that Applicant believes may be set forth as independent claims without need of importing additional limitations or elements from other embodiments or aspects set forth herein for interpretation or clarification other when explicitly set forth in such independent claims once written. It is also understood that any variations of the aspects set forth herein represent individual and separate features that may be individually added to independent claims or dependent claims to further define an invention being claimed by those respective dependent claims should they be written.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. An apparatus for sensing at least one volatile organic compound (VOC), comprising:
   a) a housing;
   b) a source of excitation radiation located within the housing, configured to direct excitation radiation onto a sample location that is within the housing, wherein the excitation radiation has a wavelength less than 300 nm;
   c) at least one optical element configured to receive emission radiation coming from the sample location, wherein the emission radiation arises from the excitation radiation, and wherein the at least one optical element within the housing directs the emission radiation along at least one detection path within the housing;
   d) at least one detector within the housing to detect the emission radiation at at least one location along the detection path;
   e) a temperature control element for modifying the temperature of the sample location from below ambient temperature to at least ambient temperature; and
   f) at least one controller configured to control operation of the source, the temperature control element, and the detector; and
   g) at least one analyzer configured to make a determination, based at least in part on the detected emission radiation, selected from the group consisting of: (1) a determination of the presence of a VOC of interest; (2) a concentration of an amount of a VOC present; and (3) both a qualitative determination of the presence of a VOC of interest and a concentration of the VOC of interest;
   wherein the controller and analyzer are selected from the group consisting of: (1) multiple electronic components; (2) a single electronic component that provides both control and analysis; (3) multiple programmable electronic components; and (4) a single programmable electron component.

2. The apparatus of claim 1 configured to allow movement of the VOC into and out of the housing while in a vapor state and wherein the temperature control element and the controller are configured to provide condensation of the VOC onto the sample location and evaporation of the VOC from the sample location.

3. The apparatus of claim 1 wherein the at least one detector, controlled by the controller, is configured to make a plurality of detections while the temperature of the sample location is being lowered over a temperature lowering time.

4. The apparatus of claim 1 wherein the source of excitation radiation is configured to be operated by the controller to apply the excitation radiation in a series of pulses, each having a pulse time.

5. The apparatus of claim 4 wherein at least one detector and the source are configured to be controllable such that at least a portion of a plurality of detections occurs between pulses of applied excitation radiation.

6. The apparatus of claim 4 wherein the source and the at least one detector are configured to be controllable such that at least a portion of a plurality of detections occurs during application of pulses of excitation radiation.

7. The apparatus of claim 1 wherein the housing has a height selected from a group of heights consisting of: (1) less than six inches; (2) less than five inches; and (3) less than four inches;
   a width selected from the group of widths consisting of: (1) less than four inches; (2) less than three inches; and (3) less than two inches; and
   a thickness selected from the group of thicknesses consisting of: (1) less than one inch; (2) less than 0.8 inches; and (3) less than about 0.6 inches; and
   wherein the apparatus additionally comprises at least one fan that is configured to provide for functionality selected from the group consisting of: (1) bringing at least one VOC into a sampling chamber that includes the sample location; (2) removing at least one VOC from a sampling chamber that includes the sample location; (3) bringing at least one VOC from a sampling chamber during a cooling down of the sample location; and (4) removing at least one VOC from a sampling chamber during a heating of the sample location.

8. The apparatus of claim 1 wherein the source comprises a device selected from the group consisting of: (1) a hollow cathode laser; (2) an LED; (3) an LET; (4) a semiconductor laser; and (5) an e-beam pumped semiconductor laser.

9. The apparatus of claim 1 wherein the source provides excitation radiation at a wavelength less than 280 nm.

10. The apparatus of claim 1 wherein the source provides excitation radiation at a wavelength less than 250 nm.

11. The apparatus of claim 1 additionally comprising a battery located within the housing for powering the source, the detector, the temperature control element, the at least one controller, and the at least one analyzer.

12. The apparatus of claim 1 wherein the emission radiation comprises native fluorescence emission radiation.

13. The apparatus of claim 1 wherein the emission radiation is selected from the group consisting of at least one of: (1) native fluorescence emission radiation, (2) Raman emission radiation, (3) phosphorescence emission radiation, (4) Rayleigh scattering, and (5) luminescence emission radiation.

14. The apparatus of claim 1 wherein the at least one detector comprises a plurality of detectors that receive the emission radiation from the sample location without use of a dispersive optical element.

15. An apparatus for detecting at least one volatile organic compound (VOC) of interest, comprising:
   a) a housing;
   b) a source of excitation radiation located within the housing, wherein the source is configured to direct the excitation radiation, having a wavelength under 300 nm, onto a sample location;
   c) at least one optical element located within the housing and configured to receive native fluorescence emission radiation from a sample location within the housing, wherein the native fluorescence emission radiation arises from the excitation radiation impinging on a sample when located at the sample location, wherein the at least one optical element is configured to direct the native fluorescence emission radiation along at least one detection path, located within the housing;
   d) a detector within the housing to detect the native fluorescence emission radiation at at least one location along the detection path; and
   e) at least one controller configured to control operation of the source and the detector;
   f) at least one analyzer configured to make a determination, based at least in part on the detected emission radiation, selected from the group consisting of: (1) a determination of the presence of the VOC of interest; (2) a concentration of an amount of the VOC of interest present; and (3) both a qualitative determination of the presence of the VOC of interest and a concentration of the VOC of interest;
   wherein the controller and analyzer are selected from the group consisting of: (1) multiple electronic components; (2) a single electronic element that provides both control and analysis; (3) multiple programmable electronic components; and (4) a single programmable electronic component.

16. The apparatus of claim 15 wherein the housing occupies a volume selected from the group consisting of: (1) less than 2.0 liters, (2) less than 1.0 liters, and (3) less than 0.5 liters.

17. The apparatus of claim 15 wherein the source supplies excitation radiation having a wavelength selected from the group consisting of: (1) less than 300 nm, (2) less than 280 nm, and (3) less than 250 nm; and
   wherein the apparatus additionally comprises a temperature modulating device, which is controlled by the controller, and which is configured to vary a temperature of the sample location such that variations in an amount of VOC at the sample location occurs.

18. An apparatus for detecting at least one volatile organic compound (VOC) of interest, comprising:
   a) a source of excitation radiation having a wavelength less than 300 nm;
   b) at least one optical element configured to receive native fluorescence emission radiation, from a sample location arising from exposure of a sample at the sample location to the excitation radiation, wherein the at least one optical element is configured to direct the native fluorescence radiation along a plurality of detection paths;
   c) a plurality of detectors with each detector located on one of the plurality of detection paths to allow detecting of the native fluorescence emission when present, wherein the plurality of detectors receive the native fluorescence emission radiation from the sample location without use of a dispersive optical element; and
   d) at least one electronic circuit configured to compare detected native fluorescence emission radiation to stored data to make a determination, based at least in part on the detected emission radiation, selected from the group consisting of: (1) a determination of the presence of a VOC of interest; (2) a concentration of an amount of a VOC present; and (3) both a qualitative determination of the presence of a VOC of interest and a concentration of the VOC of interest.

19. The apparatus of claim 18 wherein the source supplies excitation radiation having a wavelength selected from the group consisting of: (1) less than 300 nm, (2) less than 280 nm, and (3) less than 250 nm; and
   wherein the apparatus additionally comprises a temperature modulating device, which is controlled by the controller, and which is configured to vary a temperature of the sample location such that variations in an amount of VOC at the sample location occurs.

* * * * *